(12) United States Patent
Weidman et al.

(10) Patent No.: US 10,273,405 B2
(45) Date of Patent: Apr. 30, 2019

(54) HIGHLY TUNABLE COLLOIDAL PEROVSKITE NANOPLATELETS

(71) Applicant: MASSACHUSETTS INSTITUTE OF TECHNOLOGY, Cambridge, MA (US)

(72) Inventors: Mark Clayton Weidman, Cambridge, MA (US); Michael Seitz, Meilen (CH); William Alfred Tisdale, Belmont, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

(21) Appl. No.: 15/585,912

(22) Filed: May 3, 2017

(65) Prior Publication Data
US 2017/0321117 A1  Nov. 9, 2017

Related U.S. Application Data

(60) Provisional application No. 62/331,952, filed on May 4, 2016.

(51) Int. Cl.
| | |
|---|---|
| C09K 11/06 | (2006.01) |
| C07F 7/24 | (2006.01) |
| H01G 9/20 | (2006.01) |
| H01L 51/52 | (2006.01) |
| C07F 7/22 | (2006.01) |
| H01L 51/00 | (2006.01) |
| C09K 11/66 | (2006.01) |
| C04B 35/515 | (2006.01) |
| C09K 11/02 | (2006.01) |

(52) U.S. Cl.
CPC .......... *C09K 11/06* (2013.01); *C04B 35/5152* (2013.01); *C07F 7/2208* (2013.01); *C07F 7/24* (2013.01); *C09K 11/025* (2013.01); *C09K 11/665* (2013.01); *H01L 51/0077* (2013.01); *C04B 2235/3201* (2013.01); *C04B 2235/3293* (2013.01); *C04B 2235/3296* (2013.01); *C04B 2235/5292* (2013.01); *C04B 2235/5454* (2013.01); *C04B 2235/768* (2013.01); *C09K 2211/181* (2013.01); *C09K 2211/188* (2013.01); *H01G 9/20* (2013.01); *H01L 51/52* (2013.01)

(58) Field of Classification Search
CPC ...... C07F 7/2216; C07F 7/24; H01L 51/0077; H01L 51/52; C09K 11/665; C09K 11/06; C09K 2211/188; C09K 2211/181; H01G 9/20
USPC .......................................................... 516/99
See application file for complete search history.

(56) References Cited

PUBLICATIONS

Gonzalez-Carrero et al., "Maximizing the Emissive Properties of CH3NH3PbBr3 Perovskite Nanoparticles," J. Mater. Chem. A, 2015, 3:9187-9193.*
Cao et al., "2D homologous Perovskites as Light-Absorbing Materials for Solar Cell Applications," Journal of the American Chemical Society, 2015,137:7843-7850.*

* cited by examiner

*Primary Examiner* — William K Cheung
(74) *Attorney, Agent, or Firm* — Steptoe & Johnson LLP

(57) ABSTRACT

Colloidal perovskite nanoplatelets can provide a material platform, with tunability extending from the deep UV, across the visible, into the near-IR. The high degree of spectral tunability can be achieved through variation of the cation, metal, and halide composition as well as nanoplatelet thickness.

14 Claims, 34 Drawing Sheets

HIGHLY TUNABLE COLLOIDAL PEROVSKITE NANOPLATELETS

CLAIM FOR PRIORITY

This application claims priority to U.S. Patent Application Ser. No. 62/331,952 filed on May 4, 2016, which is hereby incorporated by reference in its entirety.

STATEMENT REGARDING FEDERALLY SPONSORED RESEARCH OR DEVELOPMENT

This invention was made with government support under Grant No. DE-SC0001088 awarded by the Department of Energy. The government has certain rights in this invention.

TECHNICAL FIELD

This invention relates to perovskite materials.

BACKGROUND

Recent progress in metal halide perovskite solar cells has highlighted many desirable properties of these semiconductor materials, including long charge carrier diffusion length, ease of fabrication, and low trap state density. See, Stranks, S. D.; Eperon, G. E.; Grancini, G.; Menelaou, C.; Alcocer, M. J. P.; Leijtens, T.; Herz, L. M.; Petrozza, A.; Snaith, H. J. *Science* 2013, 342, 341-344, Xing, G.; Mathews, N.; Sun, S.; Lim, S. S.; Lam, Y. M.; Grätzel, M.; Mhaisalkar, S.; Sum, T. C. *Science* 2013, 342, 344-347, Green, M. A.; Ho-Baillie, A.; Snaith, H. J. *Nature Photon.* 2014, 8, 506-514, De Wolf, S.; Holovsky, J.; Moon, S.; Löper, P.; Niesen, B.; Ledinsky, M.; Haug, F.; Yum, J.; Ballif, C. *J. Phys. Chem. Lett.* 2014, 5, 1035-1039, Shi, D.; Adinolfi, V.; Comin, R.; Yuan, M.; Alarousu, E.; Buin, A.; Chen, Y.; Hoogland, S.; Rothenberger, A.; Katsiev, K.; Losovyj, Y.; Zhang, X.; Dowben, P. A.; Mohammed, O. F.; Sargent, E. H.; Bakr, O. M. *Science* 2015, 347, 519-522, Stranks, S. D.; Snaith, H. J. *Nature Nanotech.* 2015, 10, 391-402, and Pazos-Outón, L. M.; Szumilo, M.; Lamboll, R.; Richter, J. M.; Crespo-Quesada, M.; Abdi-Jalebi, M.; Beeson, H. J.; Vrućinić, M.; Alsari, M.; Snaith, H. J.; Ehrler, B.; Friend, R. H.; Deschler, F. *Science* 2016, 351, 1430-1433, each of which is incorporated by reference in its entirety. The rapid advancement in perovskite solar cells has also led to a renewed interest in nanostructured and colloidal perovskite-based materials. See, Schmidt, L. C.; Pertegas, A.; Gonzalez-Carrero, S.; Malinkiewicz, O.; Agouram, S.; Espallargas, G. M.; Bolink, H. J.; Galian, R. E.; Perez-Prieto, J. *J. Am. Chem. Soc.* 2014, 136, 850-853, Dou, L.; Wong, A. B.; Yu, Y.; Lai, M.; Kornienko, N.; Eaton, S. W.; Fu, A.; Bischak, C. G.; Ma, J.; Ding, T.; Ginsberg, N. S.; Wang, L.-W.; Alivisatos, A. P.; Yang, P. *Science* 2015, 349, 1518-1521, Tyagi, P.; Arveson, S. M.; Tisdale, W. A. *J. Phys. Chem. Lett.* 2015, 6, 1911-1916, Sichert, J. A.; Tong, Y.; Mutz, N.; Vollmer, M.; Fischer, S.; Milowska, K. Z.; Cortadella, R. G.; Nickel, B.; Cardenas-Daw, C.; Stolarczyk, J. K.; Urban, A. S.; Feldmann, J. *Nano Lett.* 2015, 15, 6521-6527, and Protesescu, L.; Yakunin, S.; Bodnarchuk, M. I.; Krieg, F.; Caputo, R.; Hendon, C. H.; Yang, R. X.; Walsh, A.; Kovalenko, M. V. *Nano Lett.* 2015, 15, 3692-3696, each of which is incorporated by reference in its entirety. While low-dimensional, layered perovskite materials have been studied in the past (see, Papavassiliou, G. C. *Prog. Solid State Chem.* 1997, 25, 125-270, Papavassiliou, G. C.; Koutselas, I. B. *Synt. Met.* 1995, 71, 1713-1714, Ishihara, T.; Takahashi, J.; Goto, T. *Phys. Rev. B* 1990, 42, 11099-11107, Mitzi, D. B. *J. Chem. Soc., Dalton Trans.* 2001, 1-12, Mitzi, D. B.; Chondroudis, K.; Kagan, C. R. *IBM J. Res. Dev.* 2001, 45, 29-45, and Mitzi, D. B. *Prog. Inorg. Chem.* 1999, 48, 1-121, each of which is incorporated by reference in its entirety), bright and colloidally stable versions of these materials have only recently been developed. See, Yuan, Z.; Shu, Y.; Xin, Y.; Ma, B. *Chem. Commun.* 2016, 52, 3887-3890, and Lignos, I.; Stavrakis, S.; Nedelcu, G.; Protesescu, L.; deMello, A. J.; Kovalenko, M. V. *Nano Lett* 2016, 16, 1869-1877, each of which is incorporated by reference in its entirety. Perovskite nanoplatelets are particularly interesting because they exhibit strong quantum confinement effects, which enable thickness-dependent property tuning. Furthermore, Quan et al. have demonstrated that nanoplatelet-based perovskite solar cells exhibit enhanced resistance to air and water exposure as compared to their bulk counterparts, likely a result of surface passivation provided by ligand species. See, Quan, L. N.; Yuan, M.; Comin, R.; Voznyy, O.; Beauregard, E. M.; Hoogland, S.; Buin, A.; Kirmani, A. R.; Zhao, K.; Amassian, A.; Kim, D. H.; Sargent, E. H. *J. Am. Chem. Soc.* 2016, 138, 2649-2655, which is incorporated by reference in its entirety.

SUMMARY

A composition can include one or more of a colloidal nanoplatelet of the formula (I):

$$L_2[ABX_3]_{n-1}BX_4 \qquad (I)$$

where L is an organic ligand, A is a monovalent metal or organic molecular cation, B is a divalent metal cation, X includes a halide, and n−1 is the number of unit cells in thickness, where n is 1, 2, 3 or 4.

In certain embodiments, the organic ligand can include octylammonium (OA) or butylammonium (BA).

In certain embodiments, the monovalent metal or organic molecular cation can include cesium (Cs), methylammonium (MA) or formamidinium (FA).

In certain embodiments, the divalent metal cation can be lead (Pb) or tin (Sn).

In certain embodiments, the halide anion can be chloride (Cl), bromide (Br), iodide (I), or combinations thereof.

In certain embodiments, the n can be 1 or 2.

In certain embodiments, wherein a peak absorption wavelength of the composition can be between near-IR and UV.

In certain embodiments, a light-emitting diode can include the composition. In certain embodiments, a solar cell can include the composition.

A method of modulating an absorption and emission spectrum of a composition can include selecting a peak absorption wavelength between near-IR and UV, synthesizing a mixture of one or more colloidal nanoplatelets of the formula (I):

$$L_2[ABX_3]_{n-1}BX_4 \qquad (I)$$

where L is an organic ligand, A is a monovalent metal or organic molecular cation, B is a divalent metal cation, X is a halide anion, and n−1 is the number of unit cells in thickness, wherein n is 1, 2, 3 or 4 and wherein the halide anion is chloride (Cl), bromide (Br), iodide (I), or combinations thereof, and where the mixture has the selected peak absorption wavelength.

In certain embodiments, the organic ligand can include octylammonium (OA) or butylammonium (BA). In certain embodiments, the monovalent metal or organic molecular cation can include cesium (Cs), methylammonium (MA) or formamidinium (FA). In certain embodiments, the divalent metal cation can be lead (Pb) or tin (Sn). In certain embodiments, the n can be 1 or 2.

Other aspects, embodiments, and features will be apparent from the following description, the drawings, and the claims.

DETAILED DESCRIPTION

Figure 1A:
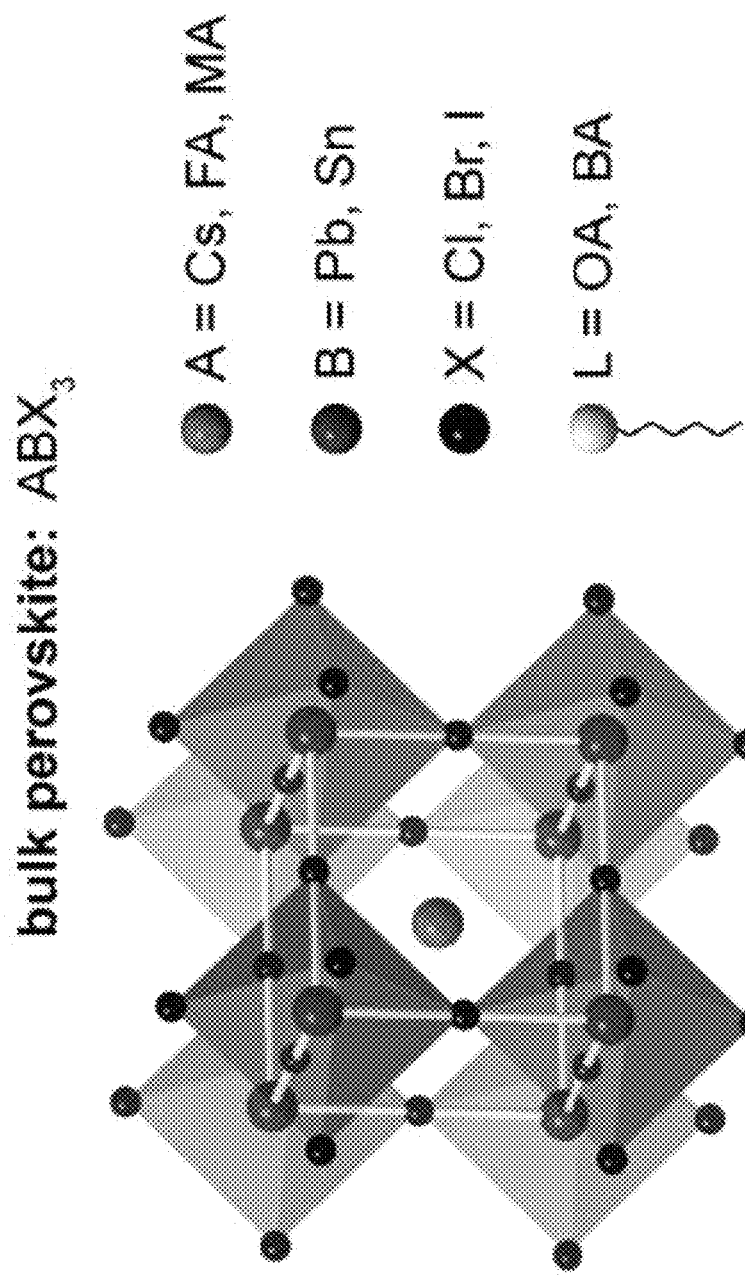
FIG. 1A shows bulk perovskite unit cell (white cube) and the chemical species used for A, B, X, and L in this study.

Colloidal perovskite nanoplatelets are a promising new class of semiconductor nanomaterials, exhibiting bright luminescence, tunable and spectrally narrow absorption and emission features, strongly confined excitonic states, and facile colloidal synthesis. Disclosed herein is the high degree of spectral tunability achievable through variation of the cation, metal, and halide composition as well as nanoplatelet thickness. Nanoplatelets of the form $L_2[ABX_3]_{n-1}BX_4$ was synthesized, where L is an organic ligand (octylammonium, butylammonium), A is a monovalent metal or organic molecular cation (cesium, methylammonium, formamidinium), B is a divalent metal cation (lead, tin), X is a halide anion (chloride, bromide, iodide), and n−1 is the number of unit cells in thickness. Variation of n, B, and X leads to large changes in the absorption and emission energy, while variation of the A cation leads to only subtle changes but can significantly impact the nanoplatelet stability and photoluminescence quantum yield (with values reaching up to 20%). Furthermore, mixed halide nanoplatelets exhibit continuous spectral tunability over a 1.5 eV spectral range, from 2.2 eV to 3.7 eV. These results demonstrate the versatility of colloidal perovskite nanoplatelets as a material platform, with tunability extending from the deep UV, across the visible, into the near-IR. In particular, the tin-containing nanoplatelets represent a significant addition to the small but increasingly important family of lead- and cadmium-free colloidal semiconductors.

The colloidal synthesis of methylammonium lead bromide ($MAPbBr_3$) perovskite nanoparticles was first reported by Schmidt et al.; producing a mixture of bulk-like nanoparticles and quantum confined nanoplatelets. See, Schmidt, L. C.; Pertegas, A.; González-Carrero, S.; Malinkiewicz, O.; Agouram, S.; Espallargas, G. M.; Bolink, H. J.; Galian, R.

E.; Pérez-Prieto, J. *J. Am. Chem. Soc.* 2014, 136, 850-853, which is incorporated by reference in its entirety. Tyagi et al. were able to isolate the nanoplatelets and demonstrated their thickness-dependent absorption and emission, with Sichert et al. showing that these nanoplatelets could be directly synthesized with control over nanoplatelet thickness. See, Tyagi, P.; Arveson, S. M.; Tisdale, W. A. *J. Phys. Chem. Lett.* 2015, 6, 1911-1916, and Sichert, J. A.; Tong, Y; Mutz, N.; Vollmer, M.; Fischer, S.; Milowska, K. Z.; Cortadella, R. G.; Nickel, B.; Cardenas-Daw, C.; Stolarczyk, J. K.; Urban, A. S.; Feldmann, J. *Nano Lett.* 2015, 15, 6521-6527, each of which is incorporated by reference in its entirety. Other recent works have extended the synthetic capabilities to include cesium lead halide ($CsPbX_3$) nanoplatelets and methylammonium lead iodide ($MAPbI_3$) nanoplatelets. See, Akkerman, Q. A.; Motti, S. G.; Srimath Kandada, A. R.; Mosconi, E.; D'Innocenzo, V; Bertoni, G.; Marras, S.; Kamino, B. A.; Miranda, L.; De Angelis, F.; Petrozza, A.; Prato, M.; Manna, L. *J.* Am. Chem. Soc. 2016, 138, 1010-1016, Bekenstein, Y; Koscher, B. A.; Eaton, S. W.; Yang, P.; Alivisatos, A. P. *J. Am. Chem. Soc.* 2015, 137, 16008-16011, Vybornyi, O.; Yakunin, S.; Kovalenko, M. V *Nanoscale* 2016, 8, 6278-6283, and Wu, X.; Trinh, M. T.; Zhu, X.-Y *J. Phys. Chem. C* 2015, 119, 14714-14721, each of which is incorporated by reference in its entirety. While these nanoplatelets are particularly promising for light-emitting applications, absolute tunability from the near-IR to the deep UV has yet to be shown.

Bulk perovskites can be described by the formula $ABX_3$, where A is a cation, B is a metal, and X is a halide. A perovskite nanoplatelet can similarly be described by the formula (I):

$$L_2[ABX_3]_{n-1}BX_4 \quad (I)$$

where L represents the ligand species which both gives the nanoplatelet colloidal stability and limits growth in one dimension of the nanoplatelet. Here, the n−1 term represents the thickness of the nanoplatelet in terms of the bulk unit cell, with n=2 corresponding to a complete perovskite unit cell and n=1 corresponding to an incomplete perovskite structure that lacks the A cation altogether. In certain embodiments, L is an organic ligand. In certain embodiments, the organic ligand is octylammonium or butylammonium. In certain embodiments, A is a monovalent metal or organic molecular cation. In certain embodiments, the monovalent metal or organic molecular cation can include cesium, methylammonium or formamidinium, In certain embodiments, B is a divalent metal cation. In certain embodiments, the divalent metal cation is lead or tin. In certain embodiments, X includes a halide. In certain embodiments, the halide anion is chloride, bromide, iodide, or combinations thereof.

A method of modulating an absorption and emission spectrum of a composition can include selecting a peak absorption wavelength between near-IR and UV, synthesizing a mixture of one or more colloidal nanoplatelets of the formula (I):

$$L_2[ABX_3]_{n-1}BX_4 \quad (I)$$

where L is an organic ligand, A is a monovalent metal or organic molecular cation, B is a divalent metal cation, X is a halide anion, and n−1 is the number of unit cells in thickness, wherein n is 1, 2, 3 or 4 and wherein the halide anion is chloride (Cl), bromide (Br), iodide (I), or combinations thereof, and where the mixture has the selected peak absorption wavelength.

In certain embodiments, the thinnest perovskite nanoplatelets, n=1 and n=2, can exhibit the greatest degree of quantum confinement and the greatest deviation from bulk properties. These nanoplatelets can most reliably be synthesized with single-thickness ensemble purity, which results in the narrowest absorption and emission linewidths. Using a facile non-solvent crystallization process, colloidally stable perovskite nanoplatelets were synthesized to show that the A, B, and X components can be tuned across a wide range of chemical species. This, in conjunction with thickness tuning, allows for modification of the absorption and emission properties from the deep UV, throughout the visible, and into the near-IR. Changes to the thickness (n), metal (B), and halide (X) lead to large changes in the absorption and emission wavelength. On the other hand, the cation (A) species has a small effect on the nanoplatelet absorption and emission energy, yet can have a large effect on the stability of the nanoplatelet and the photoluminescence quantum yield (PLQY). Formamidinium is an excellent cation for nanoplatelets, with narrow emission and increased PLQY over methylammonium. Furthermore, it is demonstrated that using mixtures of the halide component is a viable method of continuously tuning the properties between the pure component states. Lastly, nanoplatelets were synthesized using tin as the metal component, which is a critical step towards lead- and cadmium-free luminescent nanoparticles. This work demonstrates the exceptional tunability of perovskite nanoplatelets and to highlight some of the most promising compositions that could find application in high performance light-emitting diodes.

Figure 1B:
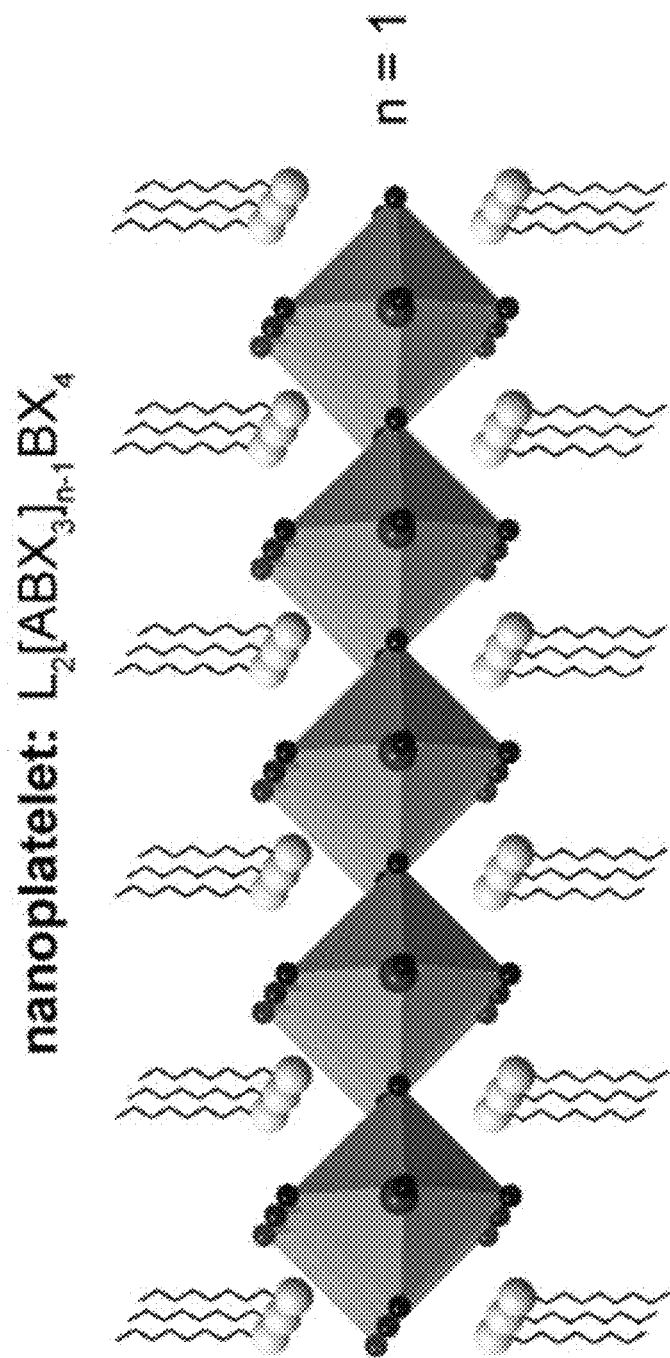
FIGS. 1B and 1C show perovskite nanoplatelets of thicknesses n=1 and n=2, where n represents the layers of metal-halide octahedra and n−1 represents the number of complete unit cells incorporated in the nanoplatelet thickness.
Figure 1C:
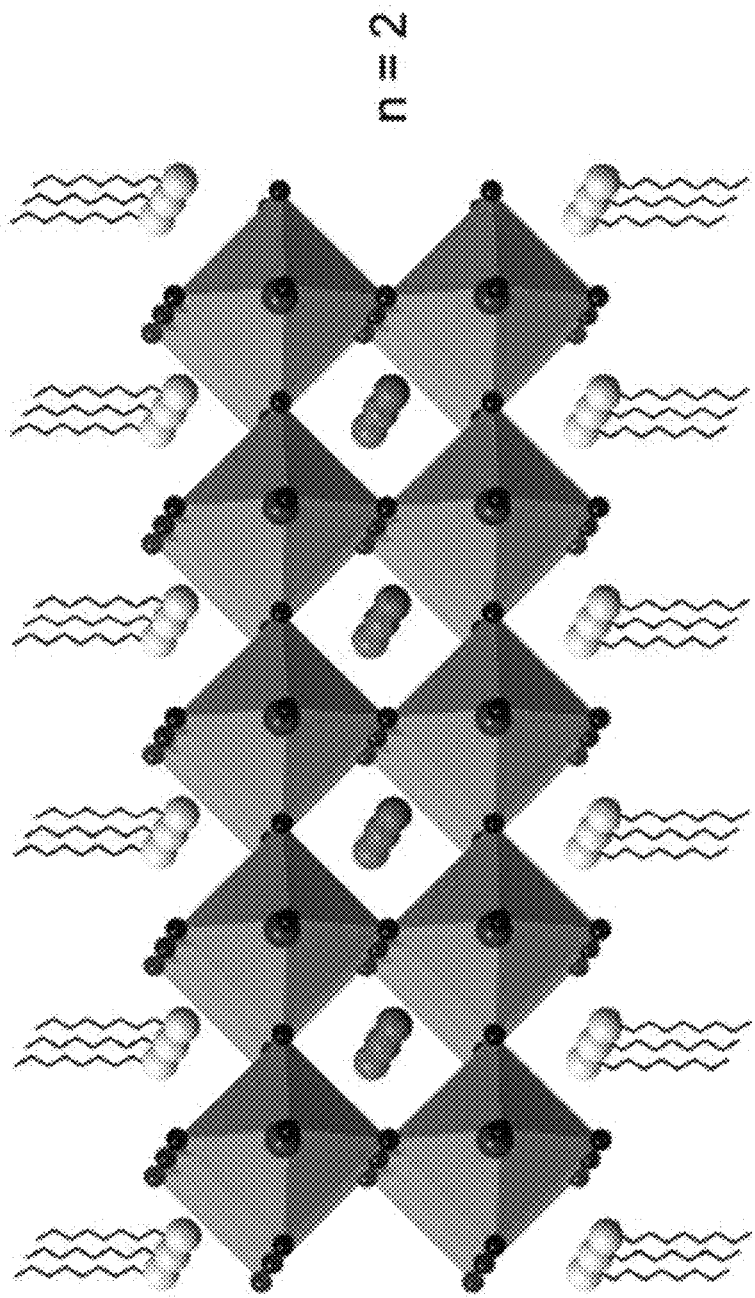
Figure 2A:
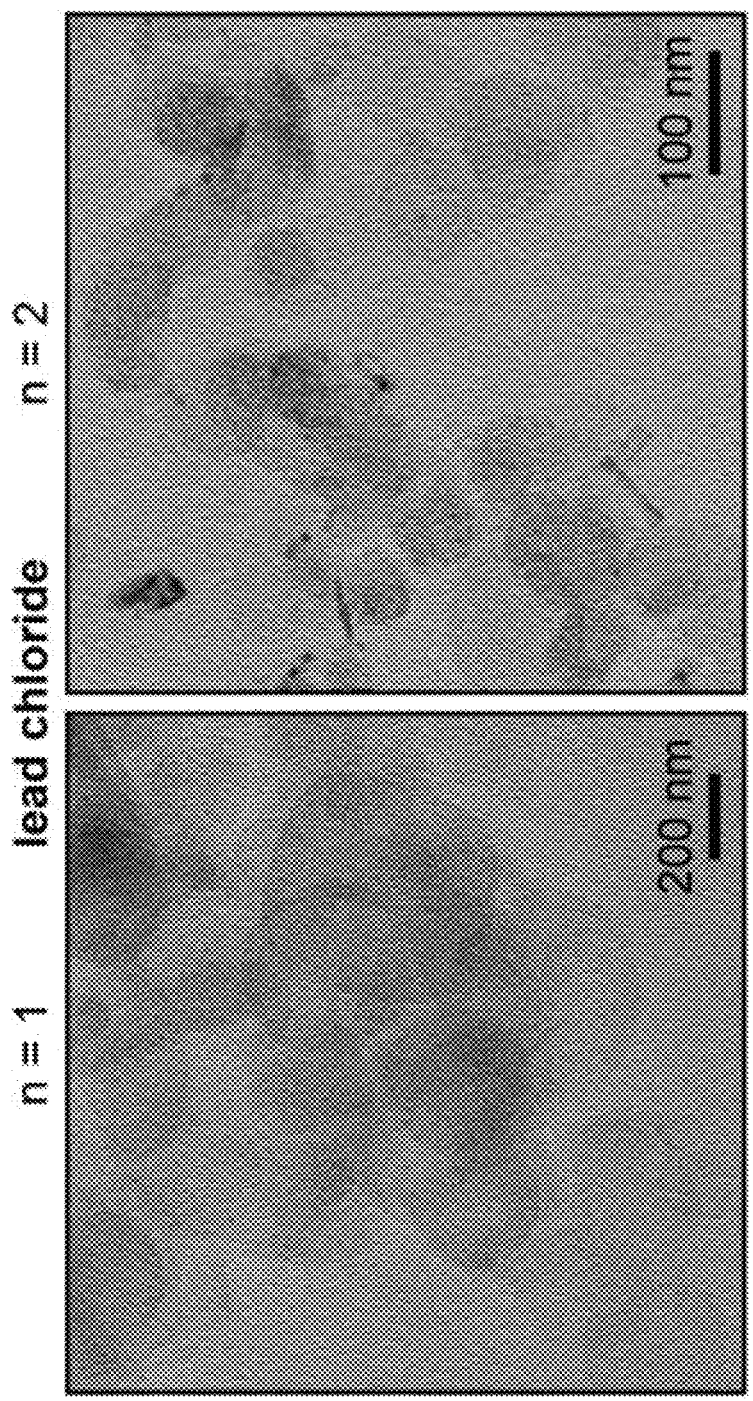
FIGS. 2A-2D show TEM images of n=1 and n=2 thickness nanoplatelets, $L_2[ABX_3]_{n-1}BX_4$, with A=FA, B=Pb or Sn, and X=Cl, Br, or I.
Figure 2B:
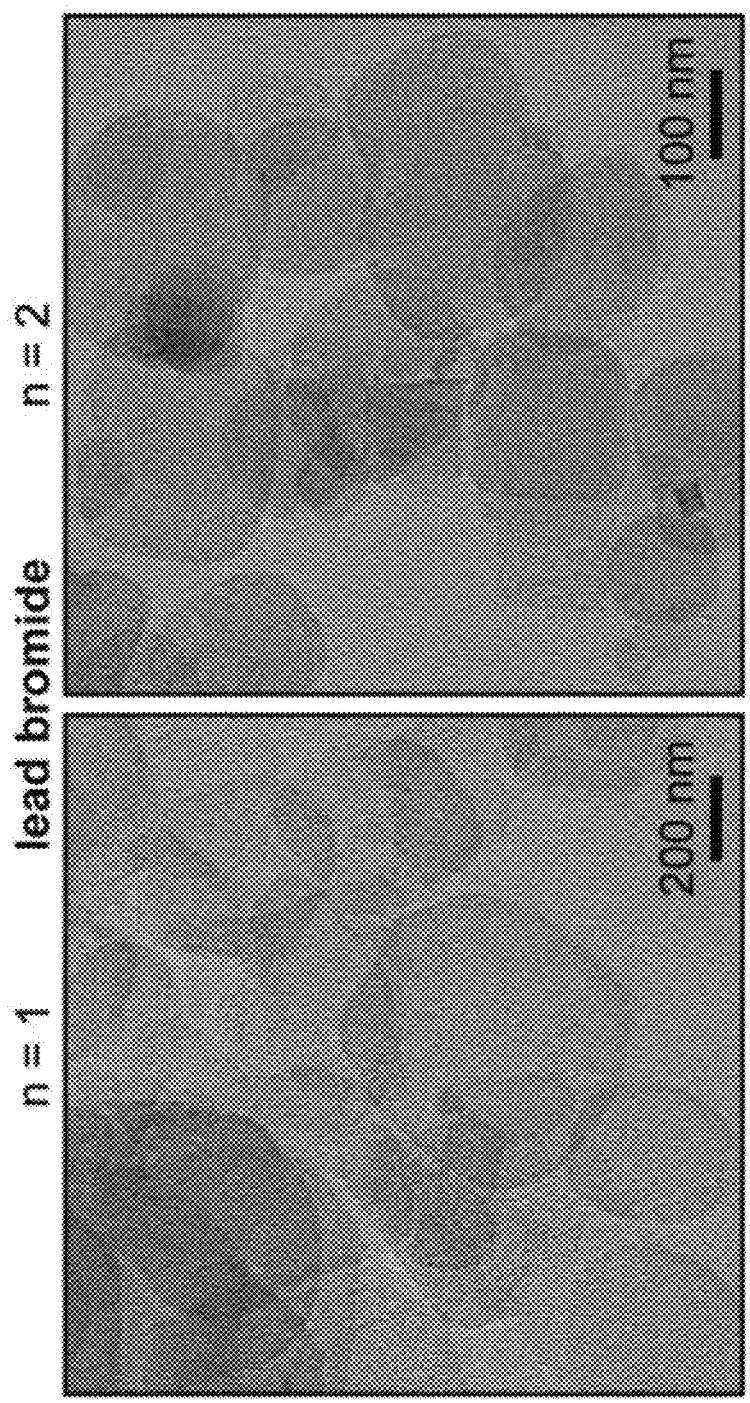
Figure 2C:
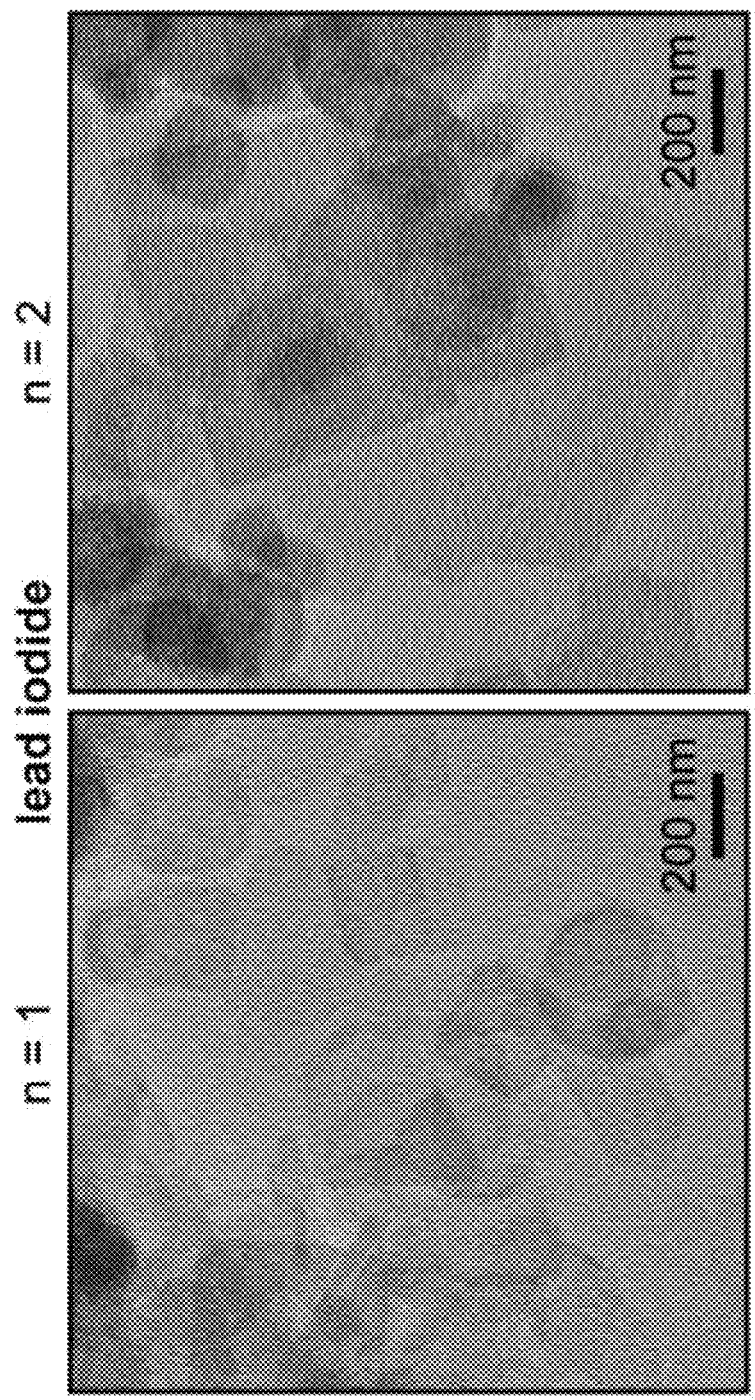
Figure 2D:
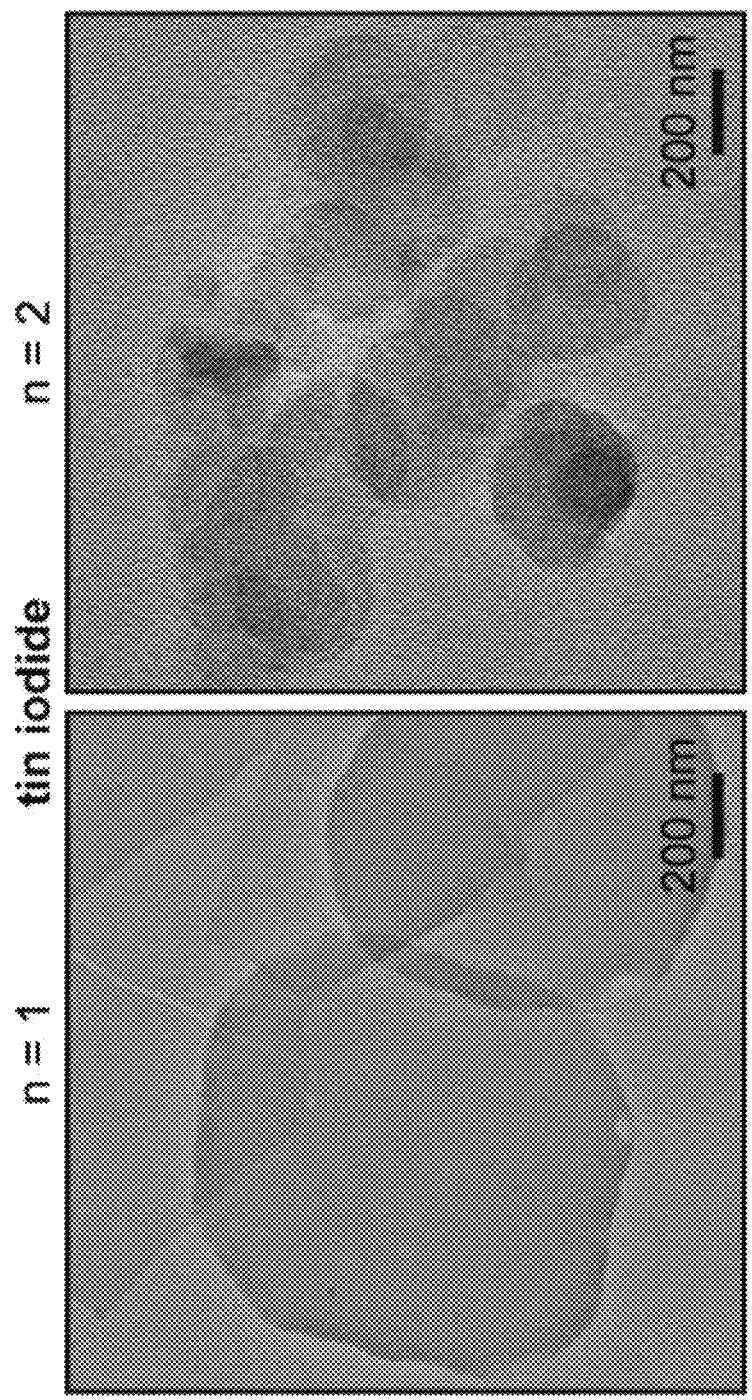

Nanoplatelet Structure. The bulk perovskite unit cell, outlined in FIG. 1A as a white cube, has the formula $ABX_3$. Typically A is a cation with +1 oxidation state, B is a metal with +2 oxidation state, and X is a halide with −1 oxidation state. Perovskite nanoplatelets, which are confined dimensionally in one direction, can be described using the formula $L_2[ABX_3]_{n-1}BX_4$, where L represents a longer chain cation which gives the nanoplatelet colloidal stability but also serves to inhibit growth of the nanoplatelet, as it is too large to fit within the unit cell geometry. See, Goldschmidt, V M. *Naturwissenschaften* 1926, 14, 477-485, and Kieslich, G.; Sun, S.; Cheetham, A. K. *Chem. Sci.* 2014, 5, 4712-4715, each of which is incorporated by reference in its entirety. Nanoplatelets with thicknesses n=1 and n=2 are depicted in FIGS. 1B and 1C, respectively. Using this notation, n represents the number of metal-halide octahedra layers present in the nanoplatelet. The number n−1 represents how many complete perovskite unit cells fit within the thickness of the nanoplatelet. Hence, for n=1 nanoplatelets, there is no cation species (A) contained within the structure.

Figure 13:
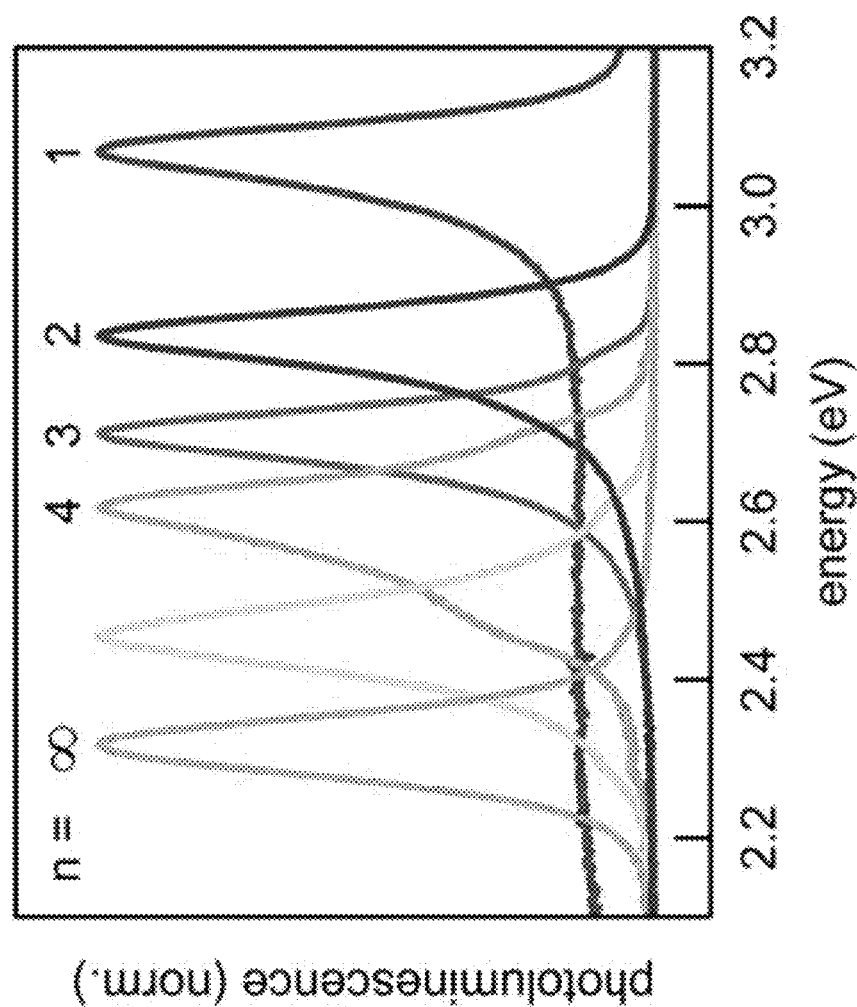
FIG. 13 shows perovskite nanoplatelets of varying thicknesses.
Figure 14:
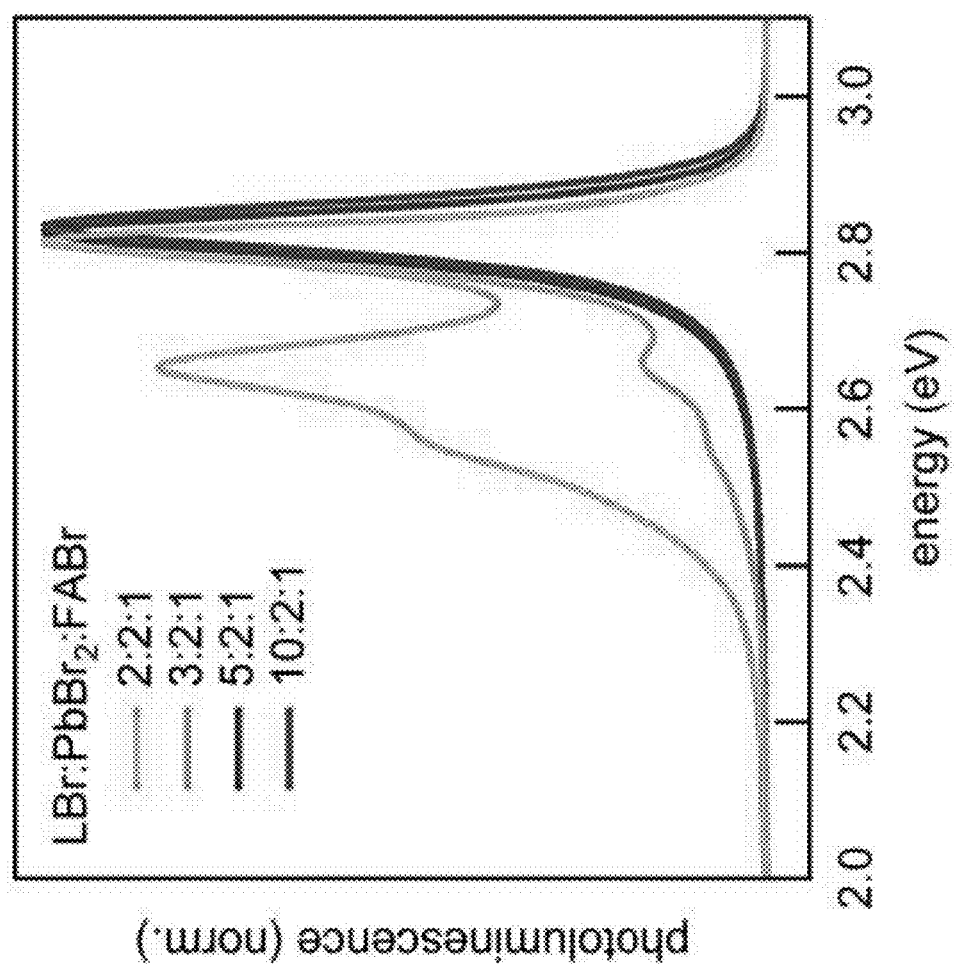
FIG. 14 shows synthesis of n=2 nanoplatelets (in this case, $L_2[FAPbBr_3]PbBr_4$) using different amounts of excess ligands (LBr, L=OA/BA mixture).

In this study, colloidal perovskite nanoplatelets (n=1 and n=2) were synthesized through the non-solvent crystallization process described in the experimental methods section. Herein n=1 and n=2 thicknesses were targeted because they can be made with the best thickness selectivity, as compared to n=3, 4, 5, etc. (see FIG. 13), which tend to result in mixtures of nanoplatelet thickness. Note the shoulders present in n>2 thickness spectra, which result from the difficulty of controlling nanoplatelet thickness homogeneity. For instance, synthesis of n=1 nanoplatelets does not include the A cation, and because the L cation is too large to pack within the $ABX_3$ unit cell, the nanoplatelet thickness is naturally confined to one layer of metal-halide octahedra. Nanoplatelets with thickness n=2 face the challenge that growth can exceed past the intended thickness, leading to more bulk-like properties. Simply using the stoichiometry dictated by n=2 (2 parts LX, 2 parts $BX_2$, 1 part AX) forms n=2 nanoplatelets but also significant quantities of thicker nanoplatelets (see FIG. 14). In FIG. 14, the stoichiometry of the nanoplatelets dictates a 2:2:1 ratio, which produces n=2 nanoplatelets (PL peak ~440 nm), but also produces thicker nanoplatelets with redshifted emission. To produce only n=2 nanoplatelets, an excess of at least 5:2:1 of ligands is required.

However, by increasing the relative concentration of the ligand (L), which inhibits growth in the confined direction, pure n=2 nanoplatelet dispersions were synthesized with excellent thickness homogeneity. Nanoplatelets with n=1 and n=2 are especially interesting because they exhibit the greatest degree of quantum confinement possible, and therefore outline the limits of thickness-dependent tunability.

Figure 17:
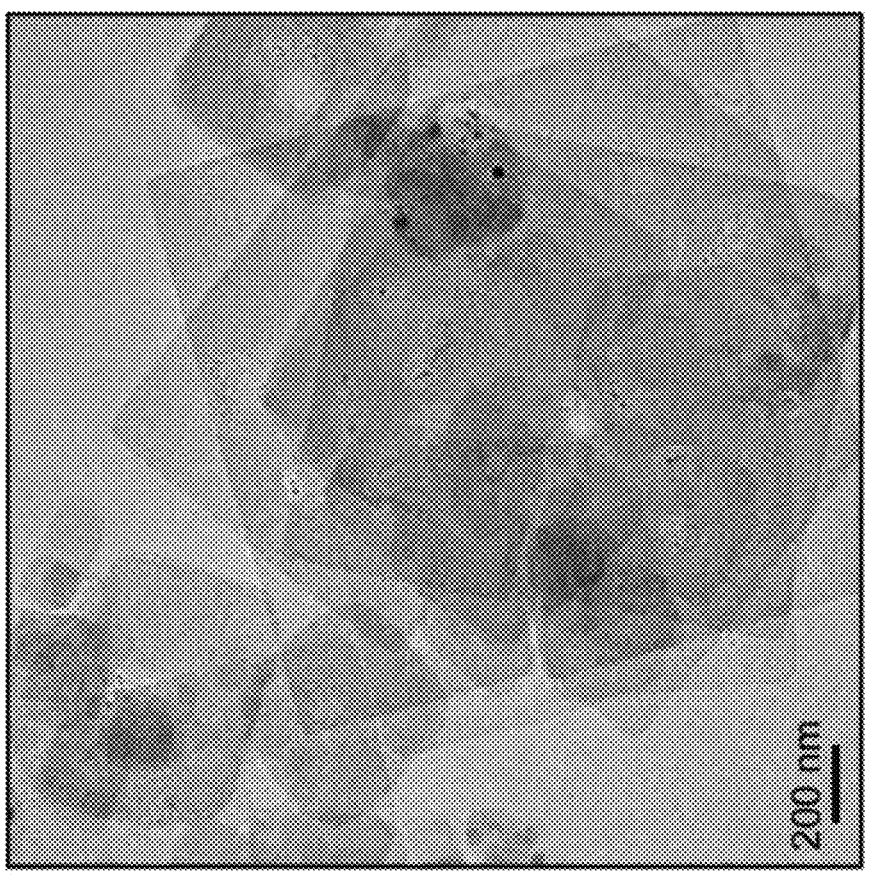
FIG. 17 shows TEM image of micron sized nanoplatelet with formula $L_2[MAPbBr_3]_2PbBr_4$.
Figure 18:
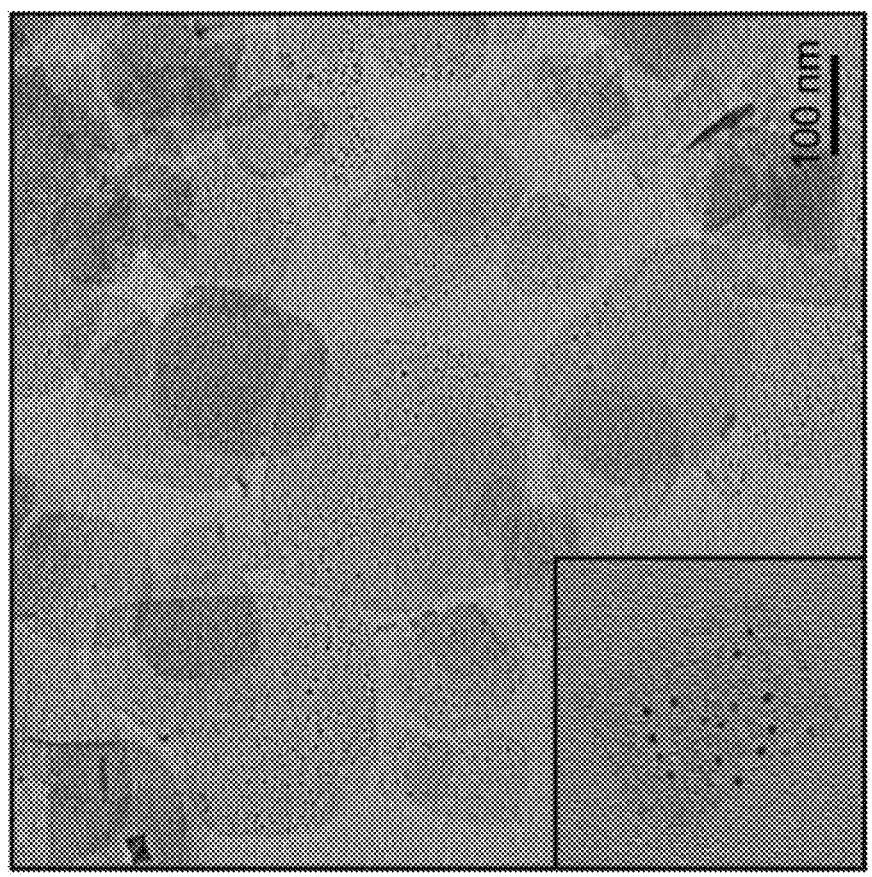
FIG. 18 shows TEM showing impurities on nanoplatelet surfaces. Nanoplatelets are $L_2[FAPbBr_3]_2PbBr_4$.
Figure 19:
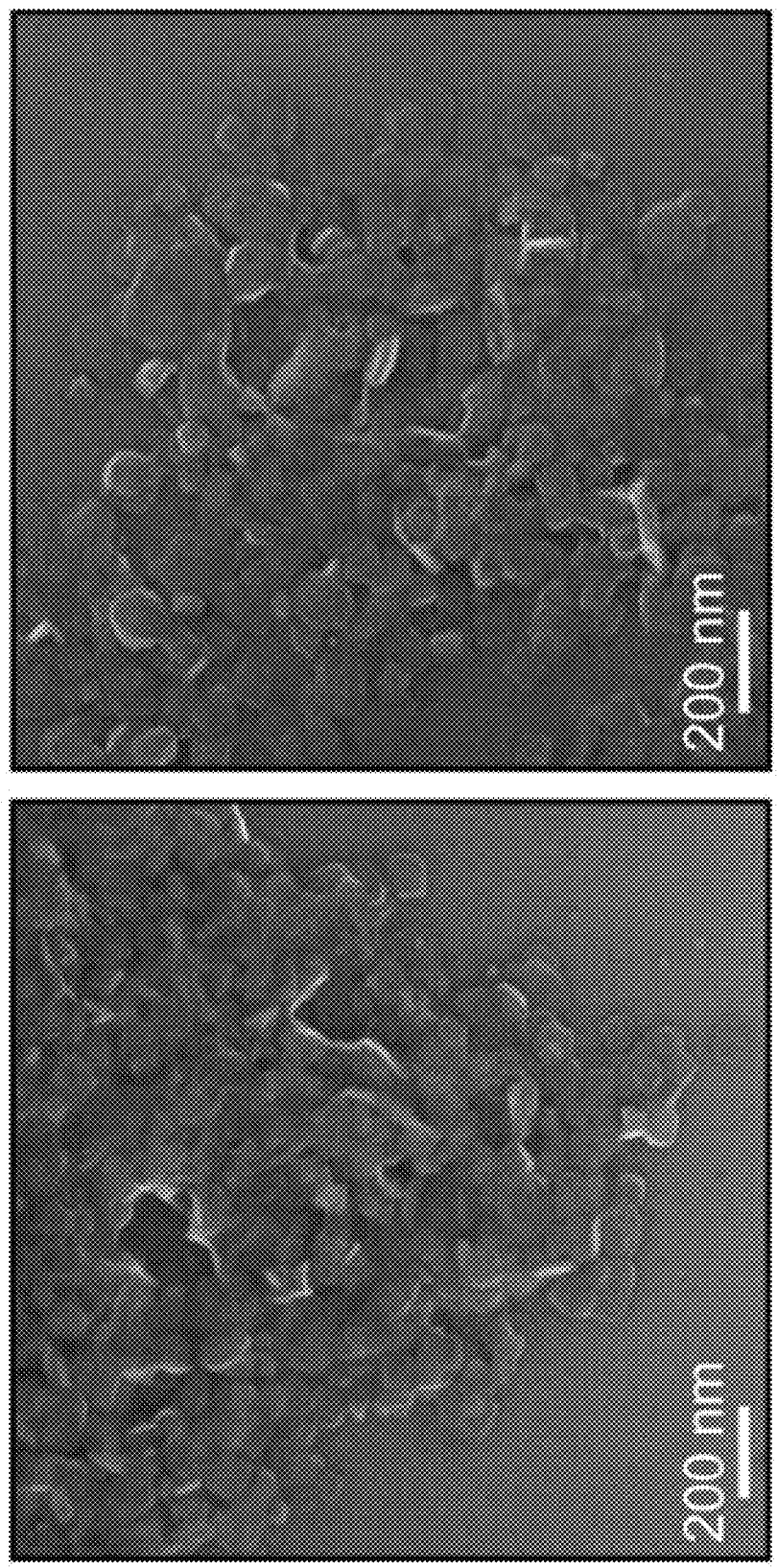
FIG. 19 shows SEM images showing clusters of $L_2[FAPbBr_3]_2PbBr_4$ nanoplatelets.

In FIGS. 2A-2D, representative TEM images were shown for the n=1 and n=2 nanoplatelets synthesized using the non-solvent crystallization method for all of the B and X configurations studied here (A was FA for all n=2 nanoplatelets). The images demonstrate the flexible nature of the synthesis, which yields similar products regardless of the chemical identities of A, B, and X. The nanoplatelets have lateral dimensions on the order of several hundred nanometers, even reaching micron scale in some cases (FIG. 17). The nanoplatelets typically have the shape of rectangles with rounded corners, however, in some cases sharper corners were observed (FIG. 17). As others have reported, dark clusters were present on the surfaces of nanoplatelets when imaged at higher magnifications (FIG. 18). However, their presence was not consistent across all nanoplatelets and their exact identity is not fully understood at this time.

Figure 3A:
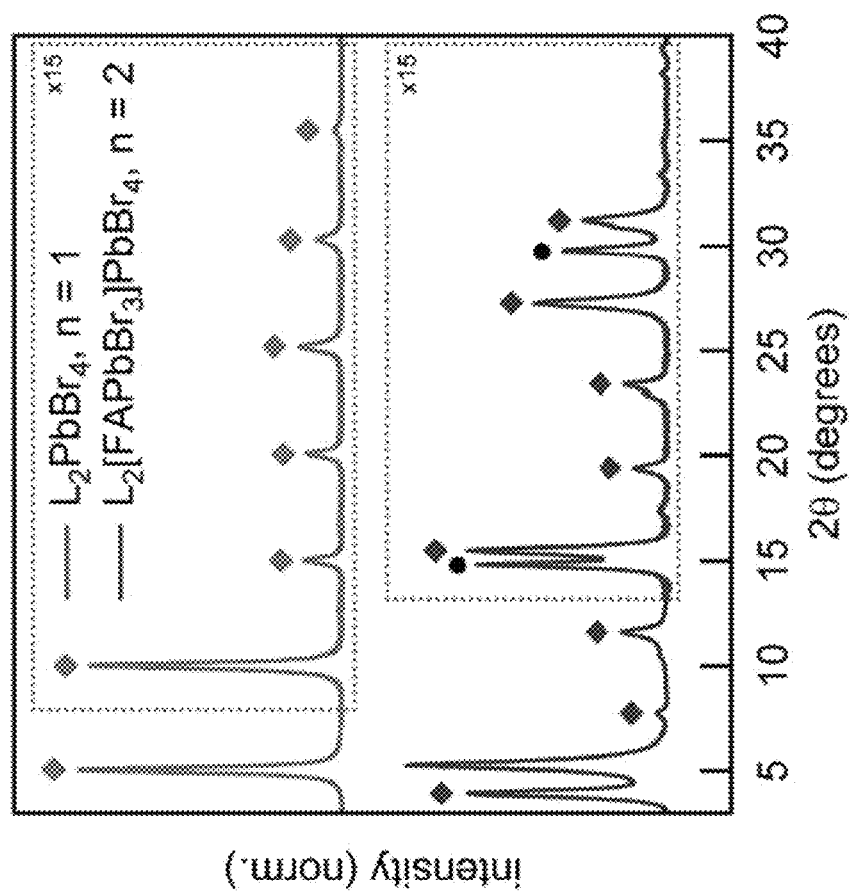
FIG. 3A shows XRD patterns for n=1 ($L_2PbBr_4$) and n=2 ($L_2[FAPbBr_3]PbBr_4$) nanoplatelets showing periodic reflections from nanoplatelet stacks which form in thin film samples (indicated by diamonds).
Figure 20:
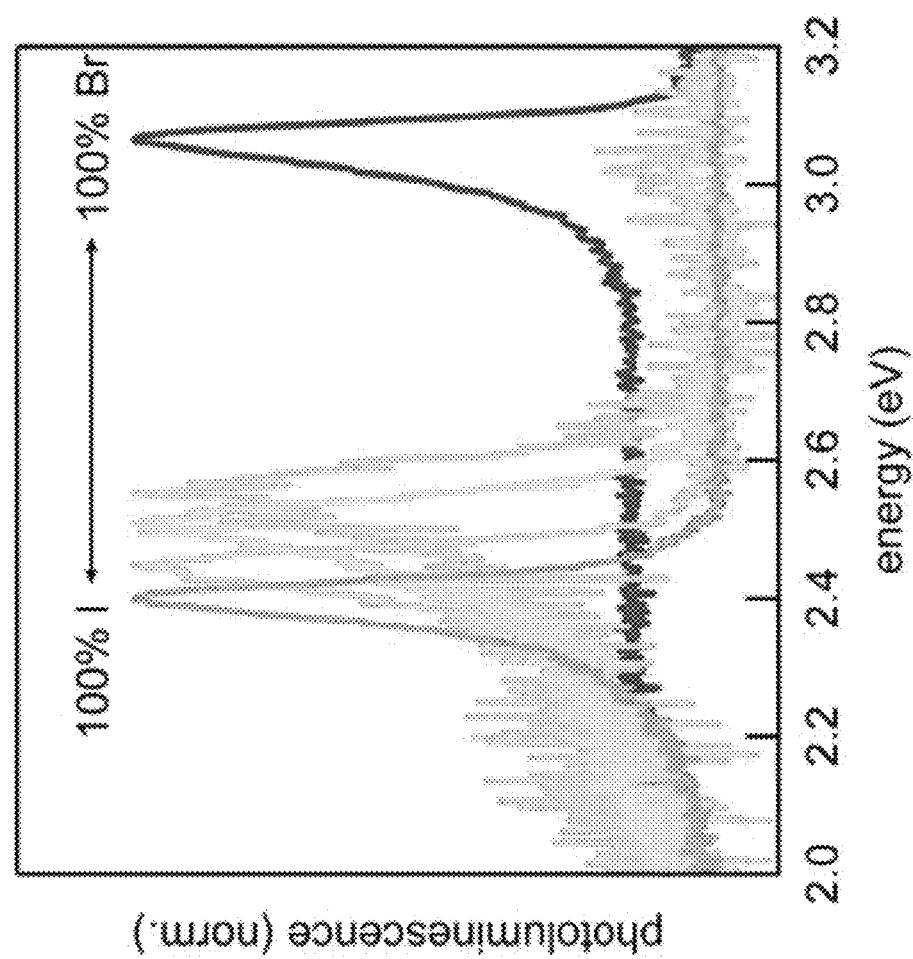
FIG. 20 shows PL spectra of n=1 nanoplatelets with mixed halide compositions.
Figure 21:
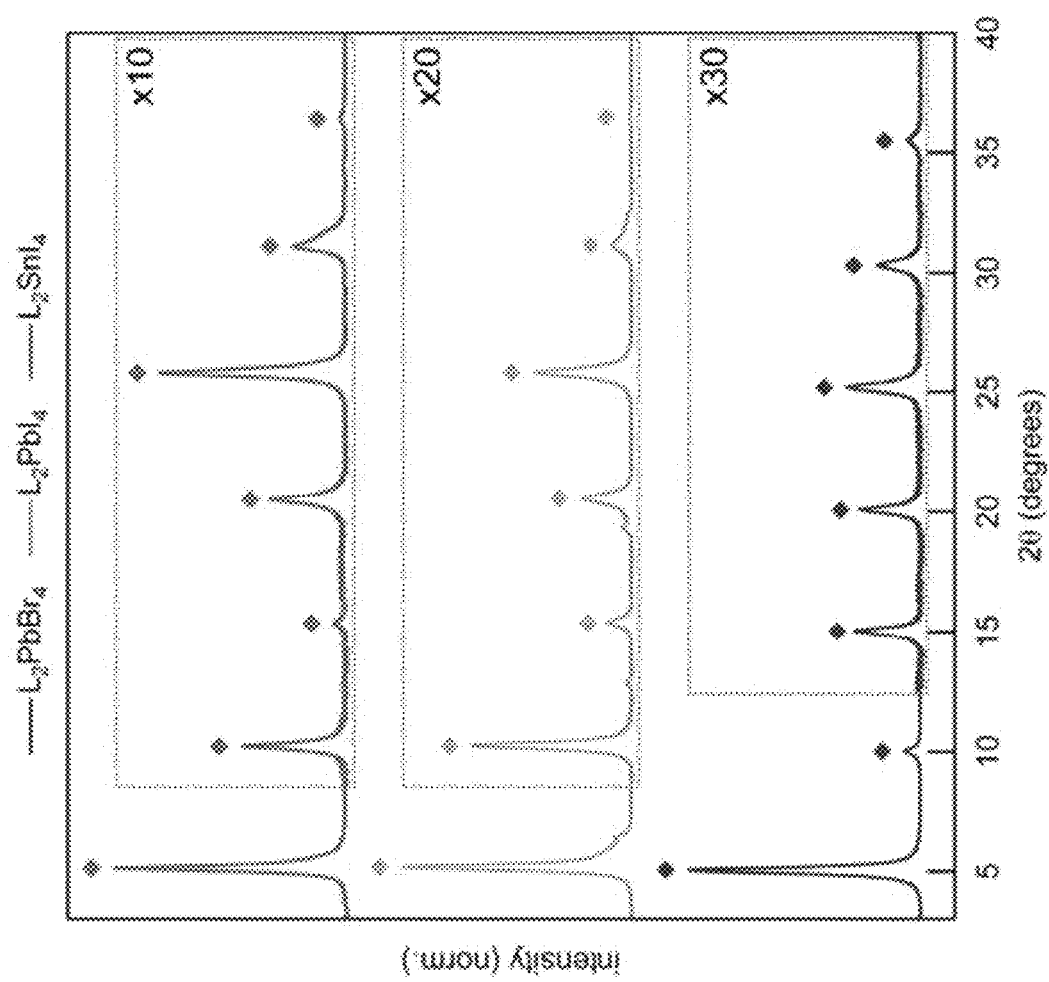
FIG. 21 shows XRD patterns for n=1 nanoplatelets showing periodicity commensurate with the average distance between stacked nanoplatelets in the film.
Figure 23:
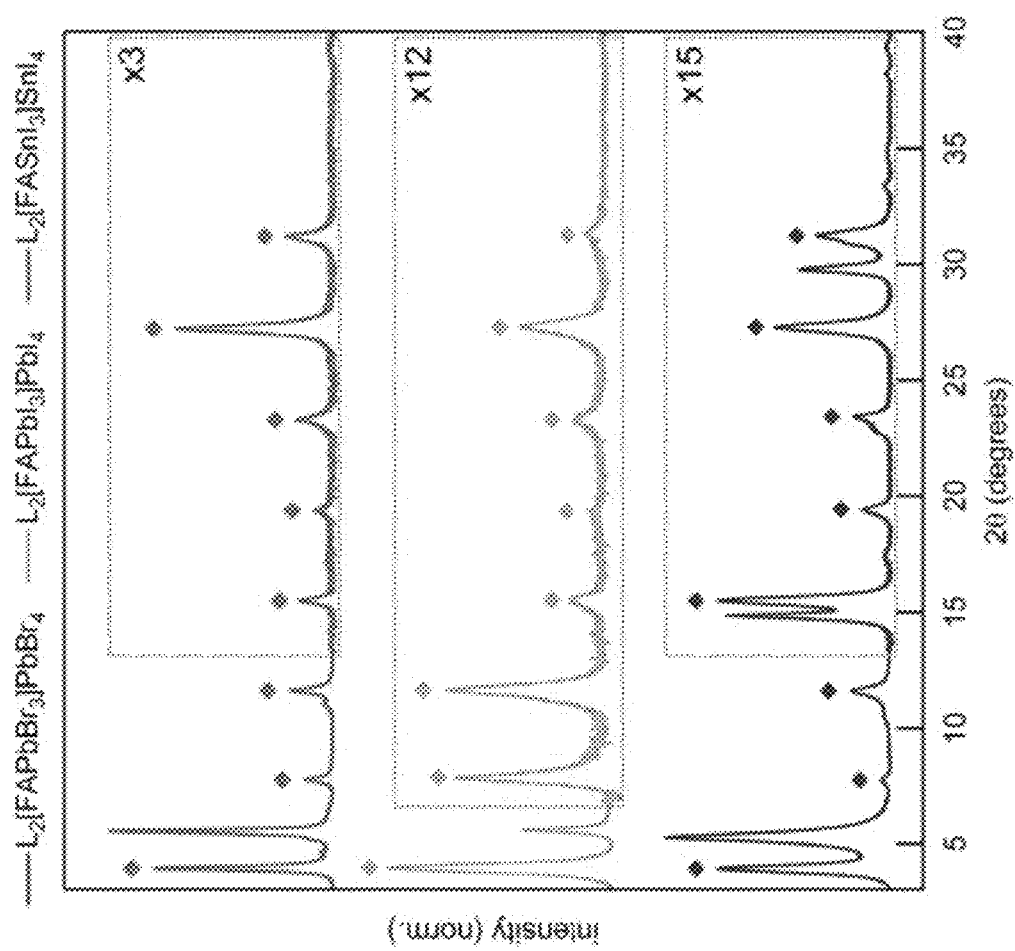
FIG. 23 shows XRD patterns for n=2 nanoplatelets showing periodicity commensurate with the average distance between stacked nanoplatelets in the film.
Figure 24:
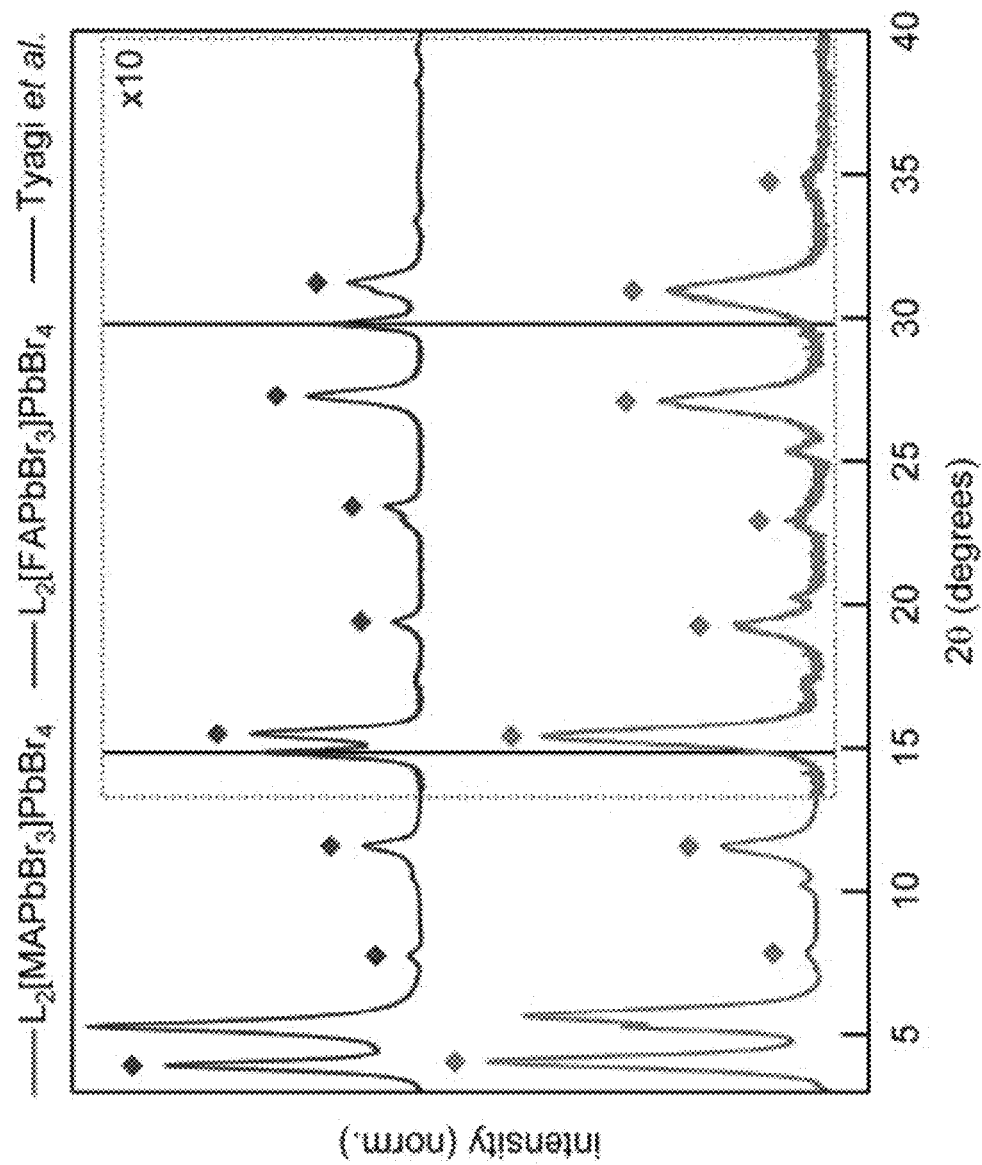
FIG. 24 shows XRD patterns for lead bromide-based n=2 nanoplatelets with either methylammonium or formamidinium.

X-ray diffraction (XRD) measurements of drop-cast thin films of nanoplatelets showed periodic diffraction at low angles indicative of nanoplatelet stacking. Typical patterns for n=1 and n=2 nanoplatelets are shown in FIG. 3A, and these were representative of all samples studied (see FIGS. 21-24). In FIGS. 21 and 23, diamonds indicate peaks at the intervals listed in Table 1. In FIG. 24, the peaks marked with diamonds are reflections from the nanoplatelet stacks, while the vertical black lines indicate the peaks from the unit cell of $MAPbBr_3$ which have previously been observed as strong reflections in nanoplatelets. See, Tyagi, P.; Arveson, S. M.; Tisdale, W. A. J. Phys. Chem. Lett. 2015, 6, 1911-1916, which is incorporated by reference in its entirety. In FIG. 3A, Black circles indicate peaks corresponding to the bulk perovskite unit cell. See, Tyagi, P.; Arveson, S. M.; Tisdale, W. A. J. Phys. Chem. Lett. 2015, 6, 1911-1916, which is incorporated by reference in its entirety. Sections of the XRD patterns have been scaled to better show the peaks at larger angles. The XRD patterns indicate a stacking distance of 1.7 nm and 2.3 nm for n=1 and n=2, respectively, regardless of chemical composition. The reflections from nanoplatelet stacks are denoted by diamonds above select peaks. It is hypothesized that the strong scattering from these superstructures is due to the large lateral dimensions of the nanoplatelets synthesized here, which forces them to lie flat when deposited in a thin film (see FIG. 20). Nevertheless, for n=2 nanoplatelets the typical peaks were observed resulting from atomic scattering of the perovskite unit cell at 14.9° and 30.1°, indicated by black circles above the peaks. See, Tyagi, P.; Arveson, S. M.; Tisdale, W. A. J. Phys. Chem. Lett. 2015, 6, 1911-1916, which is incorporated by reference in its entirety. The peaks from nanoplatelet stacking are at regular intervals of 5.1° and 3.9° for the n=1 and n=2 nanoplatelets, respectively. These periodicities correspond to average spacing between layered nanoplatelets of 1.7 nm for n=1 and 2.3 nm for n=2 nanoplatelets. The spacing is quite consistent regardless of the chemical composition of the nanoplatelets (see Table 1).

Figure 22:
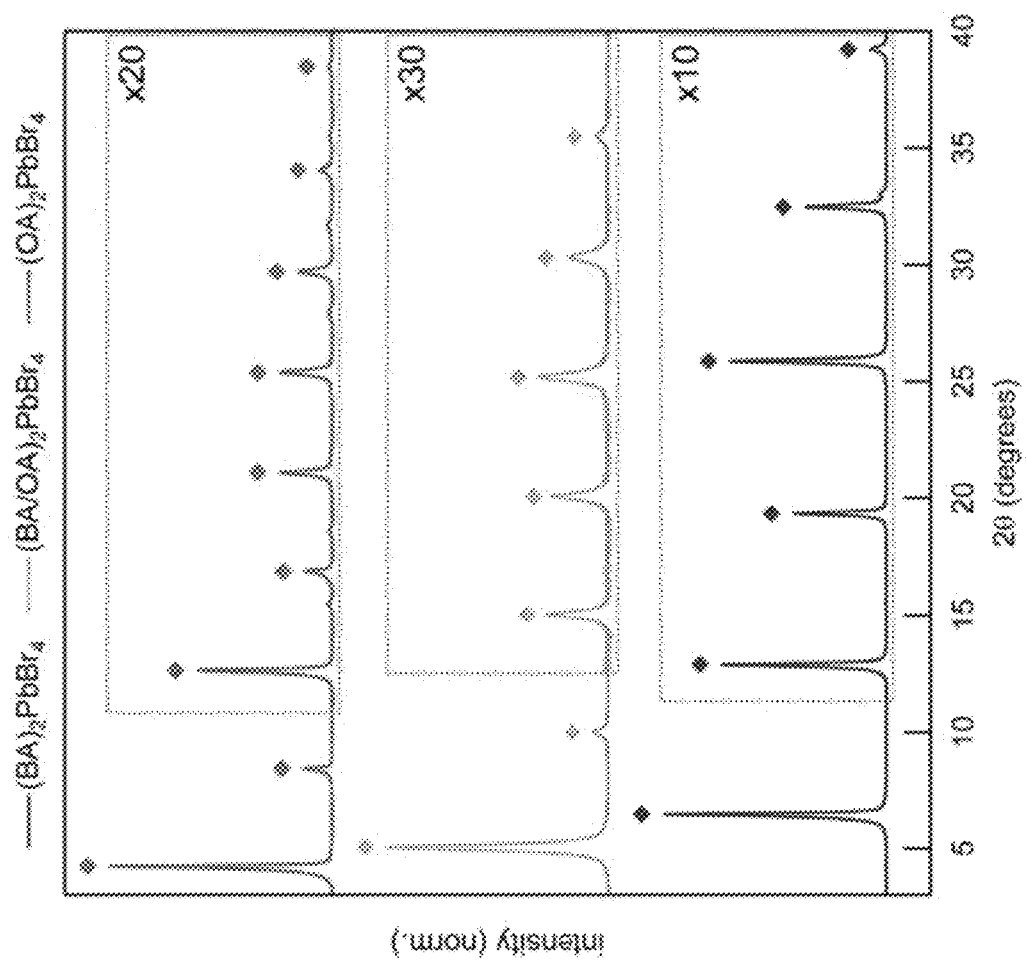
FIG. 22 shows XRD patterns for n=1 nanoplatelets with different ligands.

FIG. 22 shows the periodicity, and therefore stacking distance between nanoplatelets, is a function of the ligand length used to synthesize the nanoplatelets. The distance between nanoplatelets increases as the ligands are changed from butylammonium to a 50/50 butylammonium/octylammonium mix to octylammonium. The periodicities of BA=6.5°, BA/OA=5.1°, OA=4.3° indicate nanoplatelet stacking distances of BA=1.3 nm, BA/OA=1.8 nm, OA=2.1 nm.

Using the periodicity of the reflections measured in FIGS. 21 and 23, it is possible to extract the average distance between stacked nanoplatelets in the films used for XRD. For the lead-based nanoplatelets, the n=1 nanoplatelet stacks are typically separated by ~1.7 nm. The metal-halide octahedron is typically 0.59-0.63 nm in these materials (see, Pathak, S.; Sakai, N.; Rivarola, F. W. R.; Stranks, S. D.; Liu, J.; Eperon, G. E.; Ducati, C.; Wojciechowski, K.; Griffiths, J. T.; Haghighirad, A. A.; Pellaroque, A.; Friend, R. H.; Snaith, H. J. Chem. Mater. 2015, 27, 8066-8075, and Dang, Y.; Zhou, Y.; Liu, X.; Ju, D.; Xia, S.; Xia, H.; Tao, X. Angew. Chem. Int. Ed. 2016, 55, 3447-3450, each of which is incorporated by reference in its entirety), which means that there is approximately 1.1 nm occupied by the ligands between the nanoplatelet stacks (see FIG. 3B). The ligands are a mixture of octylammonium (~1 nm) and butylammonium (~0.5 nm), which is consistent with the observed spacing values. For the n=2 nanoplatelets, a spacing was calculated to be 2.3 nm for lead-based nanoplatelets. Assuming the same ligand spacing as the n=1 nanoplatelets (1.1 nm), this indicates the perovskite part is 1.2 nm, which is 1 unit cell greater than the n=1 nanoplatelets, or approximately the thickness of 2 metal halide octahedra layers (see FIG. 3C).

TABLE 1

XRD reflections from stacked nanoplatelets.

| formula | n | 2θ periodicity (°) | d-spacing (nm) |
|---|---|---|---|
| $L_2PbBr_4$ | 1 | 5.07 | 1.76 |
| $L_2PbI_4$ | 1 | 5.22 | 1.72 |
| $L_2SnI_4$ | 1 | 5.21 | 1.73 |
| $L_2[MAPbBr_3]PbBr_4$ | 2 | 3.84 | 2.29 |
| $L_2[FAPbBr_3]PbBr_4$ | 2 | 3.89 | 2.28 |
| $L_2[MAPbI_3]PbI_4$ | 2 | 3.92 | 2.26 |
| $L_2[FAPbI_3]PbI_4$ | 2 | 3.90 | 2.27 |
| $L_2[FASnI_3]SnI_4$ | 2 | 3.89 | 2.28 |

Figure 3C:
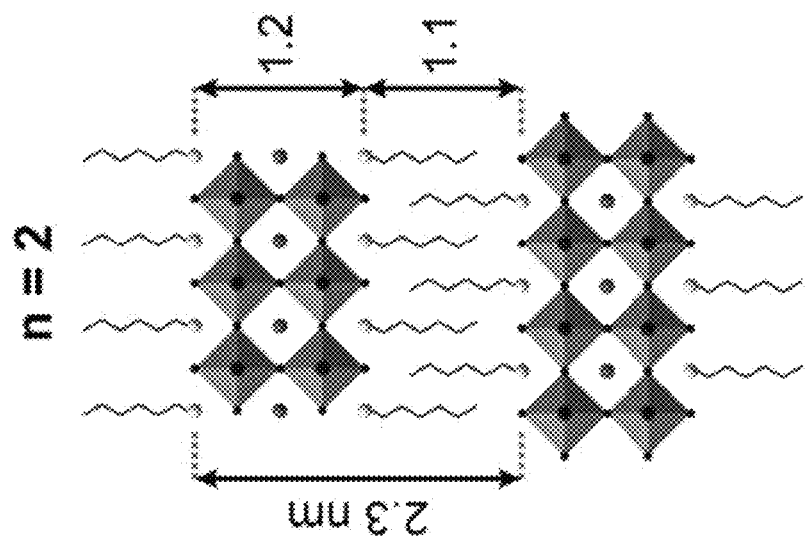
FIGS. 3B and 3C show schematic representations of the nanoplatelet stacks and relevant distances.
Figure 3B:
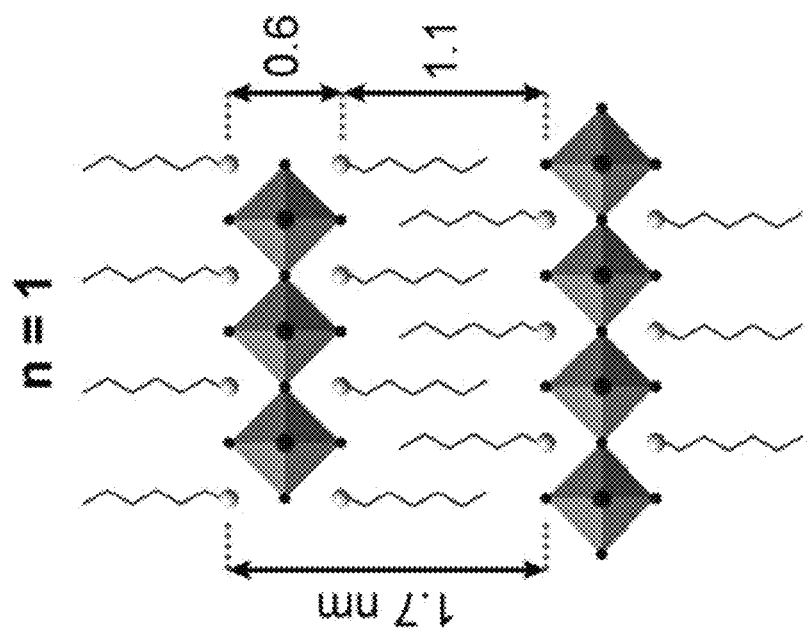

The n=1 nanoplatelets stack with an average spacing of 1.7 nm. As these nanoplatelets were made without any cation (A) species which can fit within the perovskite unit cell, the nanoplatelet consists of a single metal halide octahedra layer, which is ~0.6 nm. See, Tyagi, P.; Arveson, S. M.; Tisdale, W. A. J. Phys. Chem. Lett. 2015, 6, 1911-1916, and Pathak, S.; Sakai, N.; Rivarola, F. W. R.; Stranks, S. D.; Liu, J.; Eperon, G. E.; Ducati, C.; Wojciechowski, K.; Griffiths, J. T.; Haghighirad, A. A.; Pellaroque, A.; Friend, R. H.; Snaith, H. J. Chem. Mater. 2015, 27, 8066-8075, each of which is incorporated by reference in its entirety. Therefore, the ligands occupy a space of ~1.1 nm. The nanoplatelet ligands are an equimolar mixture of octylammonium (~1.0 nm) and butylammonium (~0.5 nm) and so this length is consistent with some ligand interdigitation between neighboring nanoplatelets. The physical picture is depicted in FIG. 3B. The n=2 nanoplatelets have an average spacing of 2.3 nm between stacks. Assuming the ligands again occupy a space of ~1.1 nm, this means the perovskite part of the nanoplatelet is ~1.2 nm thick, or 2 metal halide octahedra layers thick, with one full unit cell contained within. This depiction is shown in FIG. 3C. Using these XRD measurements, it is confirmed that the n=2 nanoplatelets are in fact 2 layers of metal halide octahedra with one full unit cell incorporated and that the nanoplatelets have not grown into thicker analogues (n>2).

Varying the Metal (B) and Halide (X) Components.

Figure 4:
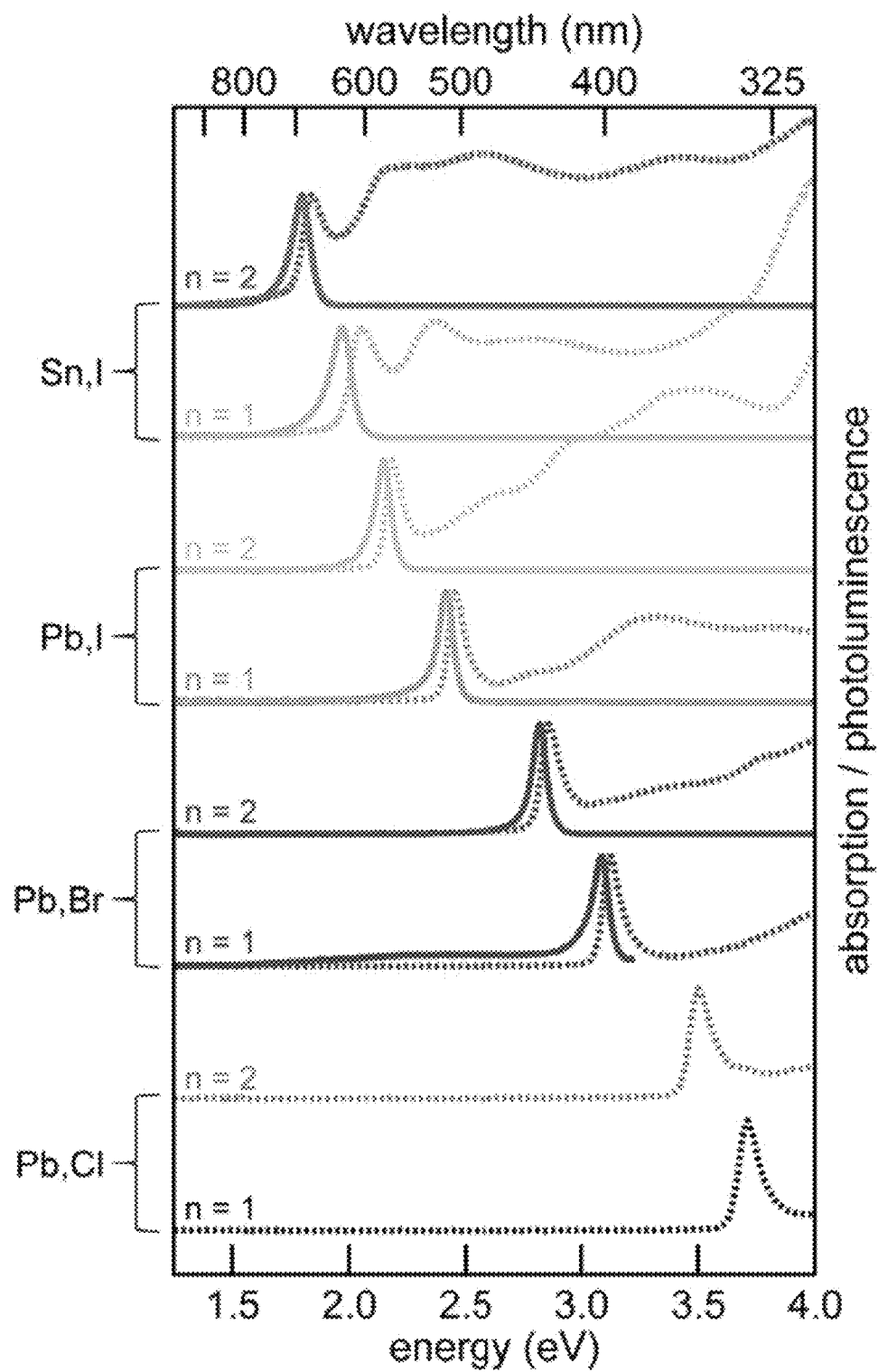
FIG. 4 shows solution phase absorption (dotted lines) and photoluminescence (solid lines) spectra for n=1 and n=2 nanoplatelets in toluene, highlighting the changes which occur when the halide (X) is changed from Cl to Br to I and when the metal (B) is changed from Pb to Sn.

As with their bulk counterparts, the A, B, and X components of the nanoplatelets to be highly tunable, providing a robust strategy for achieving a desired absorption and photoluminescence peak position. Many species for A (Cs, MA, FA), B (Pb, Sn), and X (Cl, Br, I) were explored. FIG. 4 presents the effects of changing the metal (B) and halide (X) species, which result in large changes to the nanoplatelet absorption and emission peaks. Starting with the X species, the n=1 and n=2 nanoplatelets of $L_2[FAPbCl_3]_{n-1}PbCl_4$ have peak absorption at 3.71 eV and 3.50 eV, respectively. The emission from these nanoplatelets was not measured, as their absorption is higher in energy than the 365 nm excitation source. By substituting bromide for chloride, the peak absorption/emission for $L_2[FAPbBr_3]_{n-1}PbBr_4$ n=1 and n=2 nanoplatelets is shifted lower in energy to 3.12/3.08 eV and 2.86/2.82 eV, respectively. Once again, substituting iodide in place of bromide, the peak absorption/emission for $L_2[FAPbI_3]_{n-1}PbI_4$ n=1 and n=2 nanoplatelets is shifted to 2.45/2.41 eV and 2.19/2.16 eV, respectively. These values are compiled in Table 2. Thus by changing the halide, it is possible to go from deep UV absorption (chlorides) to violet/blue emission (bromides) to green/yellow emission (iodides). In a similar fashion, by substituting Sn for Pb, the peak absorption/emission for $L_2[FASnI_3]_{n-1}SnI_4$ n=1 and n=2 nanoplatelets is shifted to 2.05/1.97 eV and 1.83/1.80 eV, respectively. As demonstrated in FIG. 4, by selection of the metal (B) and halide (X) it is possible to tune the absorption/emission of n=1 and n=2 nanoplatelets to span the entire visible region of the spectrum.

TABLE 2

Summary of absorption and emission properties of perovskite nanoplatelets ($L_2[ABX_3]_{n-1}BX_4$) and bulk, polycrystalline perovskite ($ABX_3$) phase (denoted n = ∞).

| Formula | n | Absorption[1] (nm) | (eV) | emission (nm) | (eV) | FWHM (meV) |
|---|---|---|---|---|---|---|
| $L_2PbCl_4$ | 1 | 334 | 3.71 | | | |
| $L_2[MAPbCl_3]PbCl_4$ | 2 | 347.5 | 3.57 | | | |
| $L_2[FAPbCl_3]PbCl_4$ | 2 | 354 | 3.50 | | | |
| $MAPbCl_3$[2] | ∞ | 390 | 3.18 | 413 | 3.00 | |
| $L_2PbBr_4$ | 1 | 398 | 3.12 | 403.2 | 3.08 | 89 |
| $L_2[CsPbBr_3]PbBr_4$ | 2 | 429 | 2.89 | 433.2 | 2.86 | 81 |
| $L_2[MAPbBr_3]PbBr_4$ | 2 | 430.5 | 2.88 | 437.3 | 2.83 | 89 |
| $L_2[FAPbBr_3]PbBr_4$ | 2 | 433.5 | 2.86 | 439 | 2.82 | 71 |
| $CsPbBr_3$[3] | ∞ | 525 | 2.36 | 527 | 2.35 | |
| $MAPbBr_3$[4] | ∞ | 530 | 2.34 | 540 | 2.30 | |
| $FAPbBr_3$[4] | ∞ | 549 | 2.26 | 548 | 2.26 | |
| $L_2PbI_4$ | 1 | 505.5 | 2.45 | 512.8 | 2.42 | 76 |
| $L_2[CsPbI_3]PbI_4$ | 2 | 553 | 2.24 | 561.1 | 2.21 | 79 |
| $L_2[MAPbI_3]PbI_4$ | 2 | 565.5 | 2.19 | 573.9 | 2.16 | 83 |
| $L_2[FAPbI_3]PbI_4$ | 2 | 566 | 2.19 | 575 | 2.16 | 76 |
| $CsPbI_3$[5] | ∞ | 717 | 1.73 | 714 | 1.74 | |
| $MAPbI_3$[6,7] | ∞ | 789 | 1.57 | 783 | 1.58 | |
| $FAPbI_3$[6] | ∞ | 838 | 1.48 | 810 | 1.53 | |
| $L_2SnI_4$ | 1 | 603.5 | 2.05 | 628.2 | 1.97 | 104 |
| $L_2[FASnI_3]SnI_4$ | 2 | 674 | 1.84 | 689 | 1.80 | 93 |
| $FASnI_3$[8] | ∞ | 880 | 1.41 | | | |

[1]nanoplatelet absorption is based on the peak location, and bulk absorption is the absorption onset as calculated by Tauc plot.
[2]see, Comin, R.; Walters, G.; Thibau, E. S.; Voznyy, O.; Lu, Z. H.; Sargent, E. H. *J. Mater. Chem. C* 2015, 3, 8839-8843, which is incorporated by reference in its entirety.
[3]see, Kulbak, M.; Cahen, D.; Hodes, G. *J. Phys. Chem. Lett.* 2015, 6, 2452-2456, and Yantara, N.; Bhaumik, S.; Yan, F.; Sabba, D.; Dewi, H. A.; Mathews, N.; Boix, P. P.; Demir, H. V.; Mhaisalkar, S. *J. Phys. Chem. Lett.* 2015, 6, 4360-4364, each of which is incorporated by reference in its entirety.
[4]see, Hanusch, F. C.; Wiesenmayer, E.; Mankel, E.; Binek, A.; Angloher, P.; Fraunhofer, C.; Giesbrecht, N.; Feckl, J. M.; Jaegermann, W.; Johrendt, D.; Bein, T.; Docampo, P. *J. Phys. Chem. Lett.* 2014, 5, 2791-2795, which is incorporated by reference in its entirety.
[5]see, Protesescu, L.; Yakunin, S.; Bodnarchuk, M. I.; Krieg, F.; Caputo, R.; Hendon, C. H.; Yang, R. X.; Walsh, A.; Kovalenko, M. V. *Nano Lett.* 2015, 15, 3692-3696, and Eperon, G. E.; Stranks, S. D.; Menelaou, C.; Johnston, M. B.; Herz, L. M.; Snaith, H. J. *Energy Environ. Sci.* 2014, 7, 982-988, each of which is incorporated by reference in its entirety.
[6]see, Eperon, G. E.; Stranks, S. D.; Menelaou, C.; Johnston, M. B.; Herz, L. M.; Snaith, H. J. *Energy Environ. Sci.* 2014, 7, 982-988, and Eperon, G. E.; Beck, C. E.; Snaith, H. *J. Mater. Horiz.* 2016, 3, 63-71, each of which is incorporated by reference in its entirety.
[7]see, Kong, W.; Ye, Z.; Qi, Z.; Zhang, B.; Wang, M.; Rahimi-Iman, A.; Wu, *H. Phys. Chem. Chem. Phys.* 2015, 17, 16405-16411, which is incorporated by reference in its entirety.
[8]see, Koh, T. M.; Krishnamoorthy, T.; Yantara, N.; Shi, C.; Leong, W. L.; Boix, P. P.; Grimsdale, A. C.; Mhaisalkar, S. G.; Mathews, N. *J. Mater. Chem. A* 2015, 3, 14996-15000, and Stoumpos, C. C.; Malliakas, C. D.; Kanatzidis, M. G. *Inorg. Chem.* 2013, 52, 9019-9038, each of which is incorporated by reference in its entirety.

Varying the Cation (A) Component.

Figure 5A:
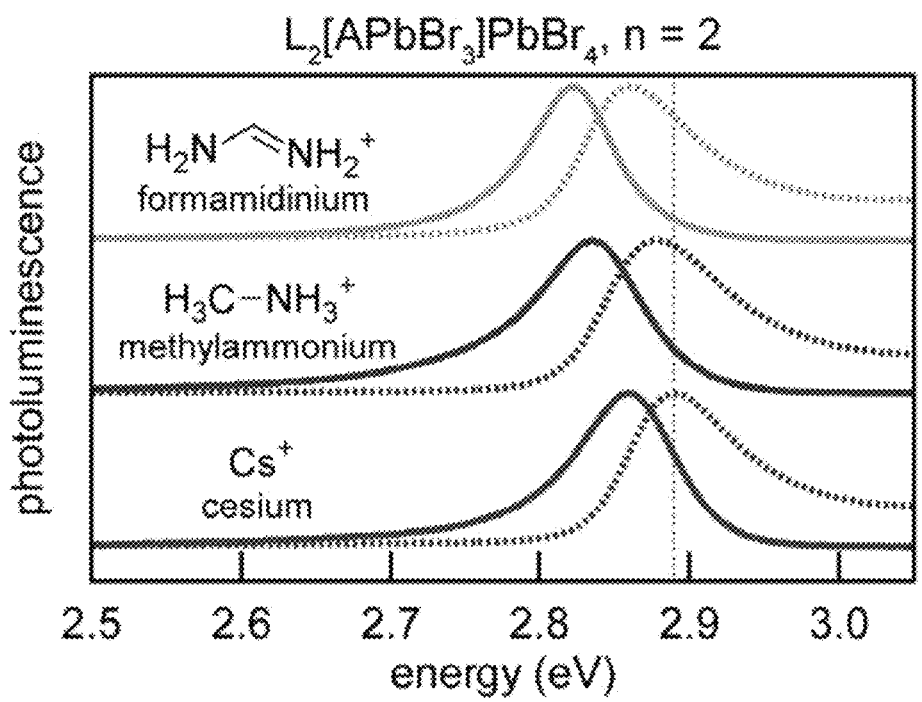
FIG. 5A shows absorption and photoluminescence spectra for n=2 nanoplatelets in toluene with varying cation (A) species for $L_2[APbBr_3]PbBr_4$ nanoplatelets and FIG. 5B shows absorption and photoluminescence spectra for $L_2[APbI_3]PbI_4$ nanoplatelets.
Figure 5B:
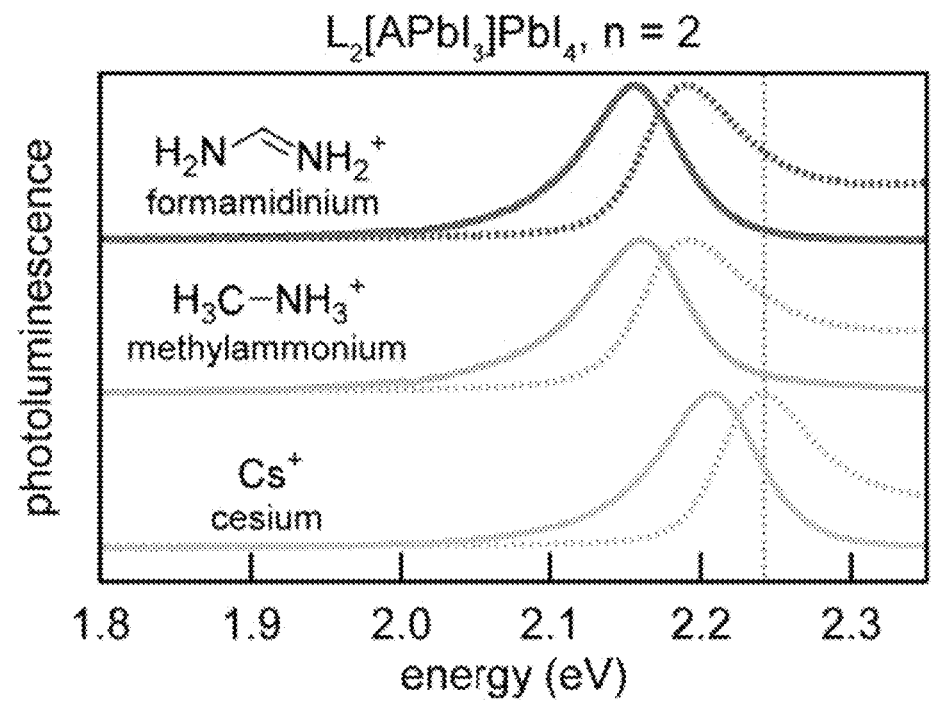
Figure 16:
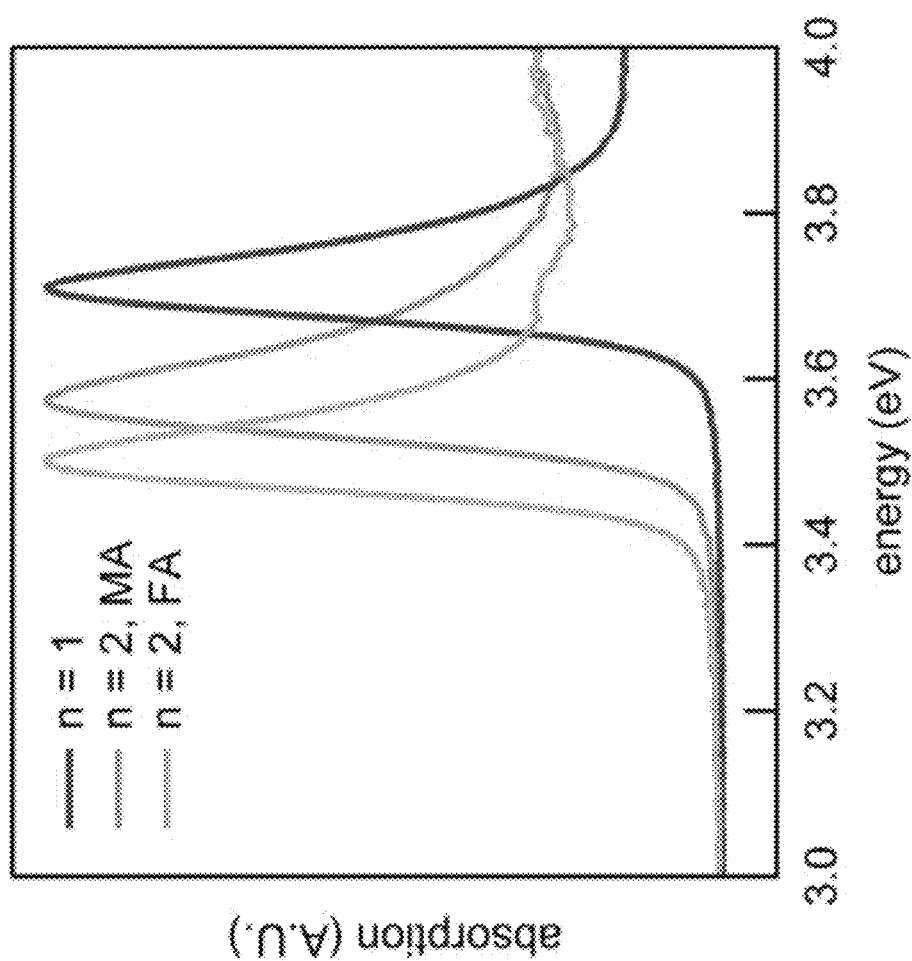
FIG. 16 shows absorption spectra from lead chloride nanoplatelets: n=1 ($L_2PbCl_4$) and n=2 ($L_2[APbCl_3]PbCl_4$) where A was methylammonium or formamidinium.

As with the B and X components, a variety of species was used for the cation (A) in n=2 nanoplatelets. However, changing the chemical identity of the cation only alters the absorption and emission energy of the nanoplatelet slightly. See, Even, J.; Pedesseau, L.; Katan, C. *Chem Phys Chem* 2014, 15, 3733-3741, and Umebayashi, T.; Asai, K.; Kondo, T.; Nakao, A. *Phys. Rev. B* 2003, 67, 155405, each of which is incorporated by reference in its entirety. FIG. 5A presents the absorption and emission of n=2 nanoplatelets, $L_2[APbBr_3]PbBr_4$, where A has been varied between Cs, MA, and FA. As the size of the cation increases (cation size: Cs<MA<FA) (see Kieslich, G.; Sun, S.; Cheetham, A. K. *Chem. Sci.* 2014, 5, 4712-4715, which is incorporated by reference in its entirety), the absorption peak shifts to slightly lower energies, in ~20 meV increments (see Table 2). This cation-dependent energy shift is also observed in the bulk phase and follows the same size-dependent trend. See, Stoumpos, C. C.; Kanatzidis, M. G. *Acc. Chem. Res.* 2015, 48, 2791-2802, and Eperon, G. E.; Stranks, S. D.; Menelaou, C.; Johnston, M. B.; Herz, L. M.; Snaith, H. J. *Energy Environ. Sci.* 2014, 7, 982-988, each of which is incorporated by reference in its entirety. FIG. 5B shows that similar behavior is observed for $L_2[APbI_3]PbI_4$ nanoplatelets, though the difference between MA and FA is less pronounced. See FIG. 16 for the absorption spectra highlighting the differences between MA and FA in lead chloride based n=2 nanoplatelets.

While changes to the cation (A) produce subtle variations in the resulting absorption and emission energy of the nanoplatelets, there are more significant implications in terms of spectral quality and photoluminescence quantum yield (PLQY). For both the bromide and iodide nanoplatelets, the FWHM of the emission peaks follow the trend of FA<Cs<MA, as listed in Table 2. In particular, MA generally leads to a more broadened emission peak (89, 83 meV) than either FA (71, 76 meV) or Cs (81, 79 meV). Furthermore, n=2 nanoplatelets synthesized with Cs tend to evolve into thicker nanoplatelets more readily than those made with MA and FA. This is attributed to the small size of the cation, which may more easily enable post-synthesis structural rearrangement within the nanoplatelet. Furthermore, the PLQY of nanoplatelets synthesized with FA, as compared to MA, tend to show higher PLQY, as listed in Table 3. In particular, the use of FA over MA provides a large boost in the PLQY of $L_2[APbBr_3]PbBr_4$ nanoplatelets, from around 6% with MA to 22% with FA. With narrow emission and high PLQY values, FA proved to be an excellent cation for nanoplatelets. Exploration of other cation species may thus be a viable pathway for increasing PLQY and stability of nanoplatelets even further. Also, n=1 nanoplatelets have reduced PLQY compared to n=2 nanoplatelets. Lastly, the tin-based nanoplatelets studied could not be diluted below and optical density of ~1 (see Supporting Information discussion of tin-based nanoplatelet synthesis), and so the PLQY values likely include absorption/reemission effects and would be an underestimate of the true PLQY. Despite this, the values for tin-based nanoplatelets are quite high when compared to bulk polycrystalline $MASnI_3$ (PLQY was below the detection limit) and $CsSnI_3$ nanoparticles (PLQY=0.06%). See, Noel, N. K.; Stranks, S. D.; Abate, A.; Wehrenfennig, C.; Guarnera, S.; Haghighirad, A.; Sadhanala, A.; Eperon, G. E.; Pathak, S. K.; Johnston, M. B.; Petrozza, A.; Herz, L. M.; Snaith, H. J. *Energy Environ. Sci.* 2014, 7, 3061-3068, and Jellicoe, T. C.; Richter, J. M.; Glass, H. F. J.; Tabachnyk, M.; Brady, R.; Dutton, S. E.; Rao, A.; Friend, R. H.; Credgington, D.; Greenham, N. C.; Bohm, M. L. *J. Am. Chem. Soc.* 2016, 138, 2941-2944, each of which is incorporated by reference in its entirety.

Figure 25:
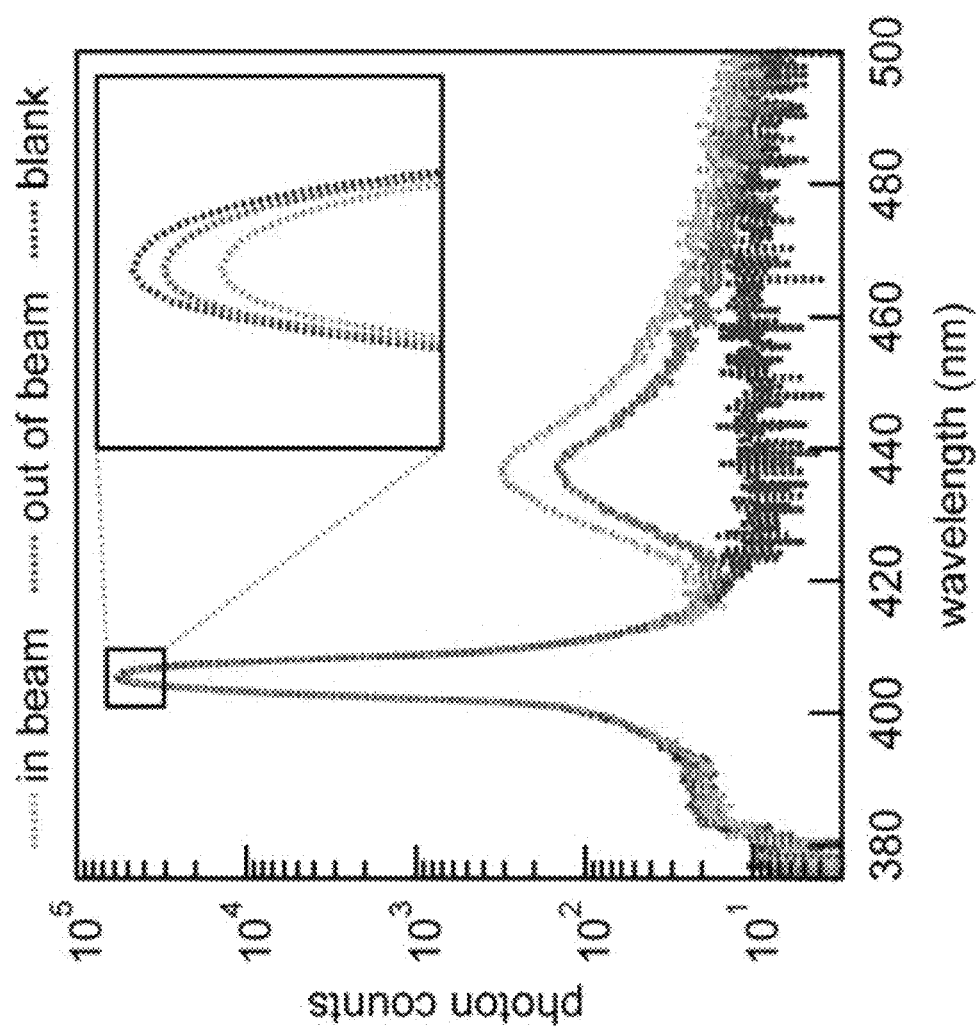
FIG. 25 shows example of the three spectra recorded for a PLQY measurement, performed using an integrating sphere.

In FIG. 25, the sample was $L_2[FAPbBr_3]PbBr_4$ nanoplatelets. The sample was suspended in toluene in a 1 cm pathlength cuvette and diluted such that the optical density at 405 nm (laser excitation wavelength) was less than 0.1. The 'in beam' measurement was with the laser passing through the cuvette, the 'out of beam' was with the laser bypassing the cuvette and striking the wall of the integrating sphere, and the 'blank' is the laser passing through a cuvette of toluene. The PLQY is then calculated as the ratio of photons emitted to photons absorbed for the first pass of the laser through the sample. See, deMello, J. C.; Wittmann, H. F.; Friend, R. H. *Adv. Mater.* 1997, 9, 230-232, which is incorporated by reference in its entirety.

TABLE 3

Photoluminescence Quantum Yield (PLQY) of Select Nanoplatelets

| Formula | n | PLQY (%) |
|---|---|---|
| $L_2[MAPbBr_3]PbBr_4$ | 2 | 6 |
| $L_2[FAPbBr_3]PbBr_4$ | 2 | 22 |
| $L_2PbI_4$ | 1 | 0.2 |
| $L_2[MAPbI_3]PbI_4$ | 2 | 1.1 |
| $L_2[FAPbI_3]PbI_4$ | 2 | 1.4 |
| $L_2SnI_4$ | 1 | 0.5* |
| $L_2[FASnI_3]SnI_4$ | 2 | 2.6* |

*these samples had OD > 1

Figure 15:
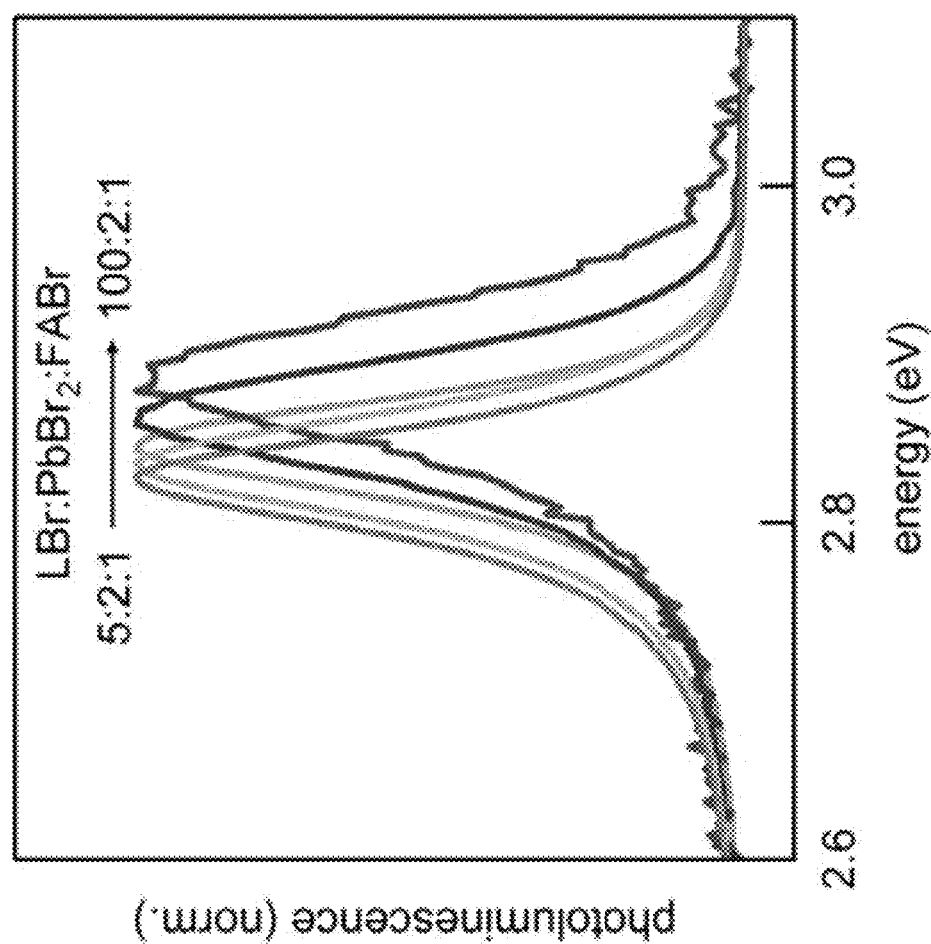
FIG. 15 shows the peak of n=2 nanoplatelets can be shifted by using larger excesses of the ligand species (LBr, L=OA/BA mixture).

The ability to readily tune the A, B, and X components of perovskite nanoplatelets makes them a highly versatile material platform. The absorption peak and emission properties of all the n, A, B, and X configurations studied here are compiled in Table 2, along with the values for their bulk polycrystalline counterparts. The values for bulk materials have been referenced from literature sources where the absorption value listed is the absorption onset as calculated by Tauc ploc, which is typically very close to the emission energy. FIG. 15 shows that the nanoplatelet emission peak can be shifted slightly as a function of the excess ligand concentration, which could explain discrepancies throughout literature for n=2 peak values and may result in some experimental variation from the listed values. The spectrum for the 100:2:1 ratio is noisy, however, this is likely due to fewer nanoplatelets being formed because of dilution rather than an indication that the photoluminescence quantum yield is less in these nanoplatelets.

Table 2 highlights the versatility of perovskite nanoplatelets as well as their narrow emission (FWHM 70-90 meV) and small Stokes shifts (30-50 meV). Their excellent properties in the blue region of the spectrum, with PLQY up to 22%, are particularly promising, as this can be a challenging region to access using other emissive nanoparticles, such as quantum dots.

Continuous Halide Tunability.

Figure 6A:
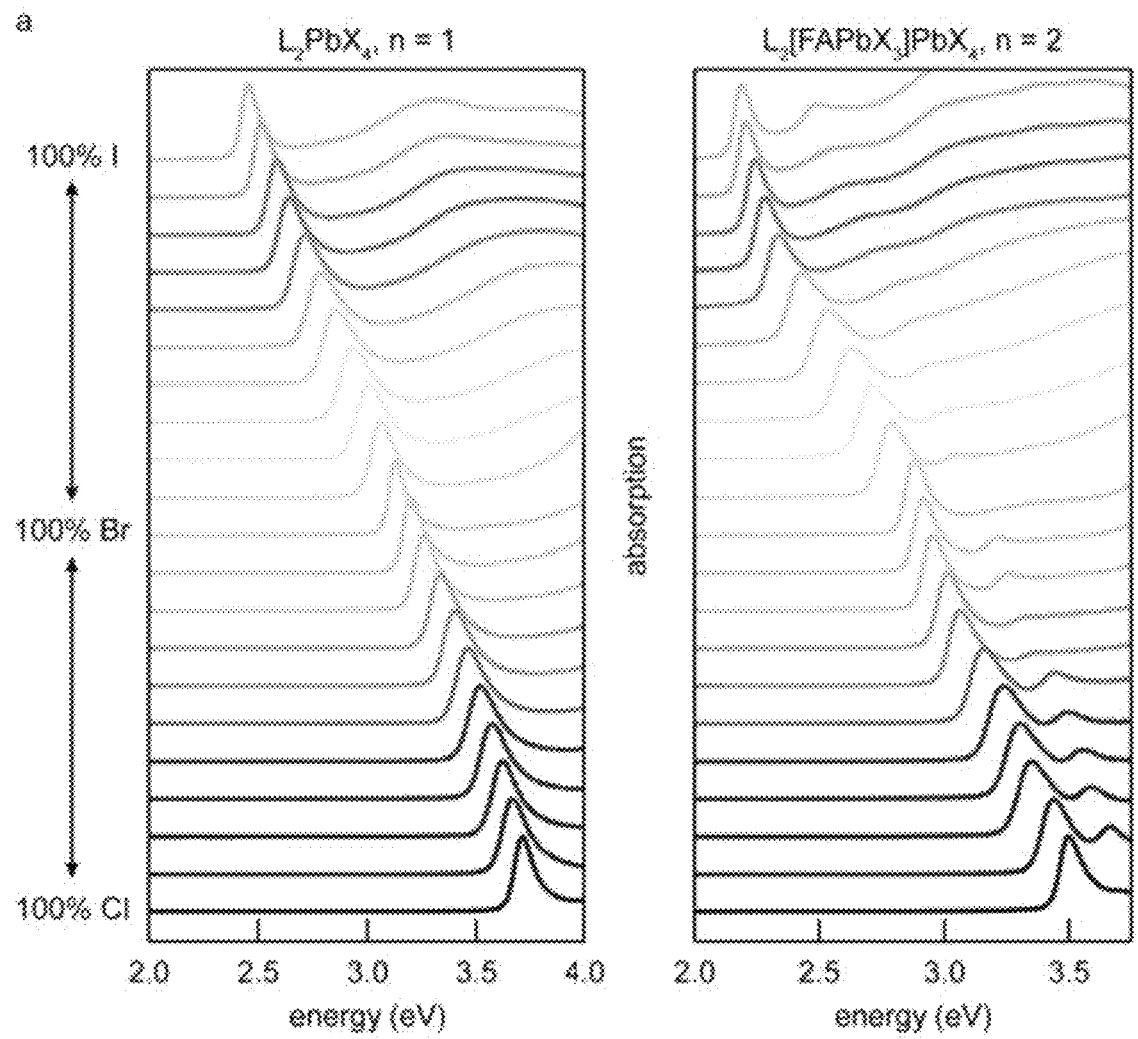
FIG. 6A shows absorption spectra for n=1 and n=2 nanoplatelets showing continuous tunability as a function of halide composition.
Figure 6B:
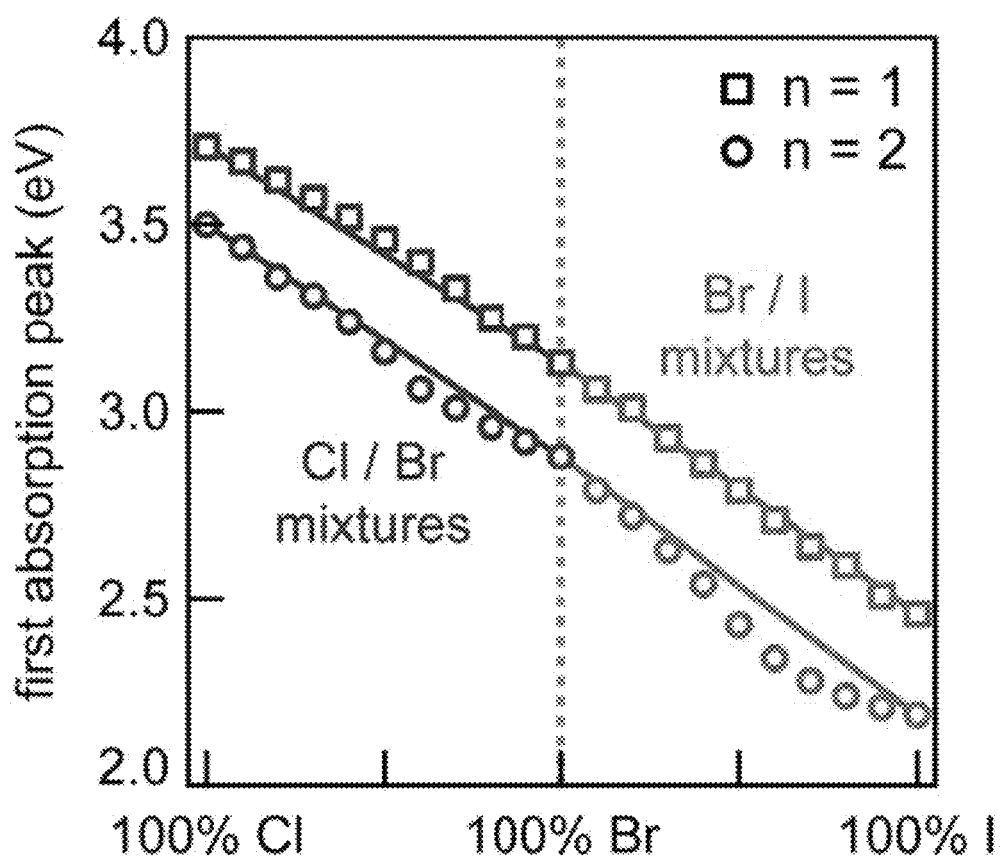
FIG. 6B shows absorption peak as a function of halide composition.
Figure 6C:
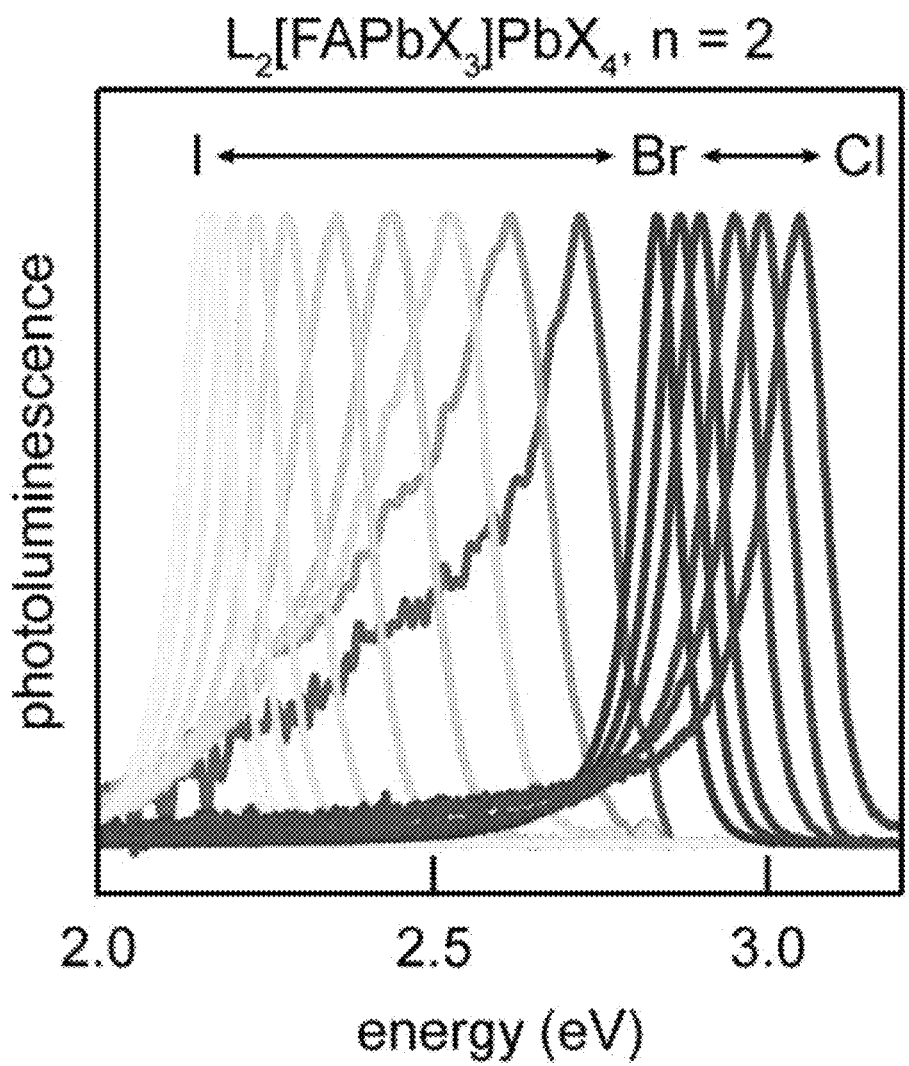
FIG. 6C shows photoluminescence of n=2 nanoplatelets for all Br/I mixtures and from 100% Br to 50/50% Cl/Br, with trace colors reflecting the color of emission.
Figure 7:
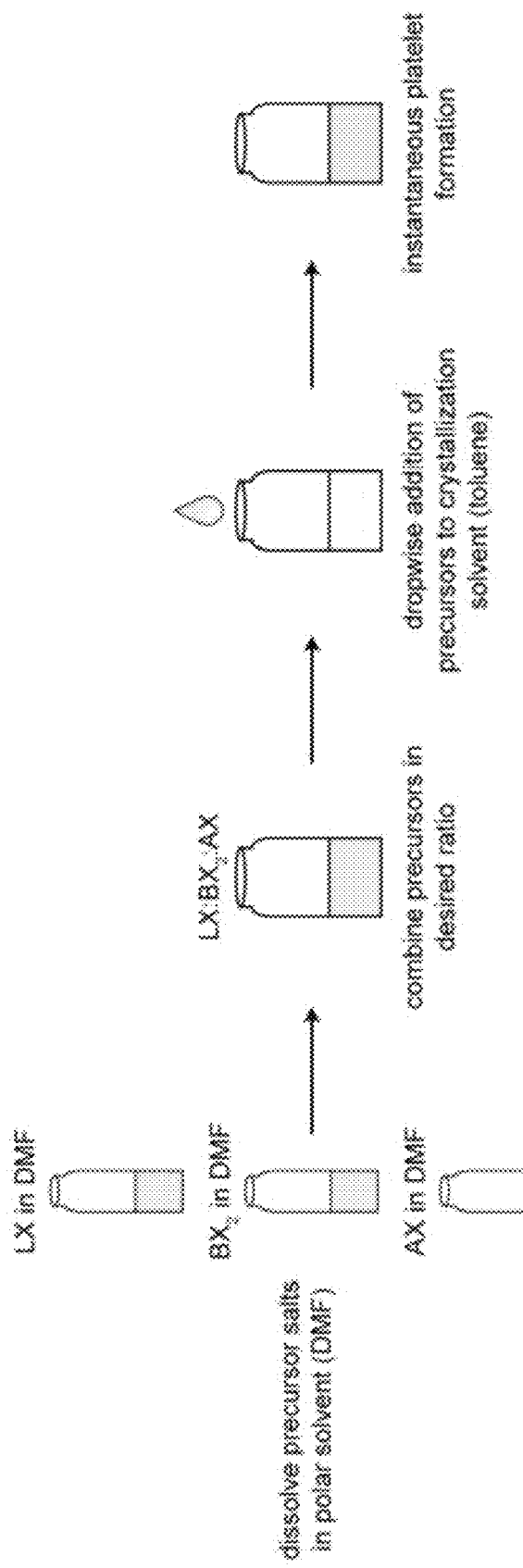
FIG. 7 shows schematic of non-solvent crystallization used for nanoplatelet synthesis.

The flexibility of the A, B, and X components in perovskite nanoplatelets allows for modification of the absorption and emission energies spanning the visible range of the spectrum and into the UV and near-IR. However, the size of these steps is either quite large (when changing the metal or halide species) or quite small (when changing the cation species). For finer control of the absorption and photoluminescence energy, FIGS. 6A-6C shows that using mixed halide compositions is a viable solution. Precursor mixtures were used to produce n=1 or n=2 nanoplatelets of pure chloride, bromide, or iodide composition. Then these solutions were mixed to make mixed halide nanoplatelets of Cl/Br or Br/I composition, in 10% increments, and synthesized nanoplatelets according to the same procedure described previously. FIG. 6A shows the absorption spectra for n=1 and n=2 nanoplatelets (A=FA, B=Pb) highlighting the excellent tunability that can be achieved using this strategy. Mixtures were made between Cl/Br and Br/I in increments of 10% between the pure compositions. All Absorption and photoluminescence measurements were taken in solution phase (toluene). In total, the absorption peak of the n=1 nanoplatelets can be tuned from 2.5 to 3.7 eV and the n=2 peak can be tuned from 2.2 to 3.5 eV. All peaks for the mixed halide compositions are single peaks and clearly different from peaks of nanoplatelets with only one halide species, proving the formation of nanoplatelets with truly mixed halide compositions.

In FIG. 6B, the energy of the absorption peak is plotted as a function of the halide composition. The solid lines are drawn between the pure halide compositions, to evaluate how closely the experimental data follow a linear trend between the absorption peak of the pure compositions (100% Cl, 100% Br, 100% I). For n=1 nanoplatelets, the absorption peak of halide mixtures closely follows its expected position based on the relative ratio of halide ions. The n=2 nanoplatelets also follow the expected trend, but some deviation from ideal behavior for bromide content between 60-80% in Cl/Br mixtures and for iodide content between 40-90% in Br/I mixtures. It has been shown by Eperon et al. that bulk $FAPb(Br_{1-x}I_x)_3$ will not crystallize in all proportions, likely due to differences in the crystal structures adopted by the pure forms (cubic for bromide, tetragonal for iodide), specifically when iodine content is in the range of 50-70% of the total halide content. See, Pathak, S.; Sakai, N.; Rivarola, F. W. R.; Stranks, S. D.; Liu, J.; Eperon, G. E.; Ducati, C.; Wojciechowski, K.; Griffiths, J. T.; Haghighirad, A. A.; Pellaroque, A.; Friend, R. H.; Snaith, H. J. *Chem. Mater.* 2015, 27, 8066-8075, and Eperon, G. E.; Stranks, S. D.; Menelaou, C.; Johnston, M. B.; Herz, L. M.; Snaith, H. *J. Energy Environ. Sci.* 2014, 7, 982-988, each of which is incorporated by reference in its entirety. While nanoplatelet formation was observed for all ratios of halide mixtures, the deviation in n=2 nanoplatelets from a linear trend may be a reflection of the behavior seen in bulk crystals.

FIG. 6C presents the photoluminescence spectra for the n=2 nanoplatelets of mixed halide compositions. The trace colors reflect the color of emission from the corresponding nanoplatelets. All mixtures of Br/I exhibit photoluminescence, although the emission from 10-30% I content nanoplatelets was weak with long low-energy tails. All mixtures of Cl/Br, which were within the detection limit, showed strong photoluminescence. This corresponds to nanoplatelets with halide compositions between 10-50% Cl. Emission was also present from some of the mixed Br/I n=1 nanoplatelets, specifically in the range of 70-90% I (see FIG. 20; from left to right: 100% I, 10% Br/90% I, 20% Br/80% I, 30% Br/70% I, 100% Br) but was generally weak. Emission from n=1 nanoplatelets with mixed Cl/Br composition is beyond the detection range. Values from FIGS. 6A-6C are available in Tables 4 and 5.

TABLE 4

Mixed halide $L_2PbX_4$ properties.

| halide composition | absorption | | emission | | |
|---|---|---|---|---|---|
| | (nm) | (eV) | (nm) | (eV) | FWHM (meV) |
| 100% Cl | 334 | 3.71 | | | |
| 90% Cl/10% Br | 338 | 3.67 | | | |
| 80% Cl/20% Br | 343 | 3.62 | | | |
| 70% Cl/30% Br | 347 | 3.57 | | | |
| 60% Cl/40% Br | 353 | 3.52 | | | |
| 50% Cl/50% Br | 359 | 3.46 | | | |
| 40% Cl/60% Br | 365 | 3.40 | | | |
| 30% Cl/70% Br | 372 | 3.33 | | | |
| 20% Cl/80% Br | 381 | 3.25 | | | |
| 10% Cl/90% Br | 388 | 3.20 | | | |
| 100% Br | 397 | 3.13 | 404 | 3.07 | 89 |
| 90% Br/10% I | 405 | 3.06 | | | |
| 80% Br/20% I | 413 | 3.01 | | | |
| 70% Br/30% I | 423 | 2.93 | | | |
| 60% Br/40% I | 434 | 2.86 | | | |
| 50% Br/50% I | 445 | 2.79 | | | |
| 40% Br/60% I | 457 | 2.71 | | | |
| 30% Br/70% I | 470 | 2.64 | 486 | 2.55 | |
| 20% Br/80% I | 480 | 2.59 | 494 | 2.51 | 125 |
| 10% Br/90% I | 493 | 2.51 | 506 | 2.45 | 95 |
| 100% I | 505 | 2.46 | 517 | 2.40 | 77 |

TABLE 5

Mixed halide $L_2[FAPbX_3]PbX_3$ properties.

| halide composition | absorption | | emission | | |
|---|---|---|---|---|---|
| | (nm) | (eV) | (nm) | (eV) | FWHM (meV) |
| 100% Cl | 354 | 3.50 | | | |
| 90% Cl/10% Br | 361 | 3.44 | | | |
| 80% Cl/20% Br | 370 | 3.36 | | | |
| 70% Cl/30% Br | 375 | 3.31 | | | |
| 60% Cl/40% Br | 383 | 3.24 | | | |
| 50% Cl/50% Br | 392 | 3.16 | 407 | 3.05 | 109 |
| 40% Cl/60% Br | 405 | 3.06 | 414 | 3.00 | 111 |
| 30% Cl/70% Br | 412 | 3.01 | 420 | 2.95 | 98 |
| 20% Cl/80% Br | 420 | 2.96 | 427 | 2.90 | 88 |
| 10% Cl/90% Br | 425 | 2.92 | 432 | 2.87 | 84 |
| 100% Br | 430 | 2.88 | 437 | 2.84 | 75 |
| 90% Br/10% I | 444 | 2.79 | 455 | 2.72 | 151 |
| 80% Br/20% I | 457 | 2.72 | 474 | 2.62 | 210 |
| 70% Br/30% I | 471 | 2.63 | 490 | 2.52 | 191 |

TABLE 5-continued

Mixed halide $L_2[FAPbX_3]PbX_3$ properties.

| halide composition | absorption | | emission | | |
|---|---|---|---|---|---|
| | (nm) | (eV) | (nm) | (eV) | FWHM (meV) |
| 60% Br/40% I | 489 | 2.54 | 508 | 2.44 | 148 |
| 50% Br/50% I | 510 | 2.43 | 526 | 2.36 | 138 |
| 40% Br/60% I | 530 | 2.34 | 543 | 2.28 | 107 |
| 30% Br/70% I | 544 | 2.28 | 554 | 2.24 | 92 |
| 20% Br/80% I | 553 | 2.24 | 563 | 2.20 | 84 |
| 10% Br/90% I | 562 | 2.21 | 570 | 2.17 | 79 |
| 100% I | 566 | 2.19 | 575 | 2.16 | 76 |

Perovskite nanoplatelets, particularly those of n=1 and n=2 thickness, show promise as a highly tunable material system. The cation (A), metal (B), and halide (X) components can be altered or mixed in many compositions to achieve a desired absorption and emission energy with excellent specificity. The ability to tune the thickness (n) is an additional dimension of flexibility over their bulk counterparts. The nanoplatelets benefit from a facile, room-temperature synthesis, efficient luminescence, and narrow absorption and emission properties. Their large lateral dimensions will permit studies of energy transfer between the nanoplatelets and other materials, such as quantum dots, and the fabrication of electronic devices. Challenges related to large-scale synthesis and long-term nanoplatelet stability must still be addressed in future studies. Tin-based nanoplatelets, if improved to be more air-stable, are especially promising as halide compositional tuning would permit the entire visible spectrum to be covered in a single, heavy-metal-free platform. See, Papavassiliou, G. C. Prog. Solid State Chem. 1997, 25, 125-270, and Peedikakkandy, L.; Bhargava, P. RSC Adv. 2016, 6, 19857-19860, each of which is incorporated by reference in its entirety. Overall, colloidal perovskite nanoplatelets represent an exciting new class of solution processable materials for tunable light absorption and emission.

EXAMPLES

Abbreviations

For ease of writing nanoplatelet compositions, the following abbreviations were used throughout to represent different chemical species. A: cesium=Cs, formamidinium=FA, methylammonium=MA. B: lead=Pb, tin=Sn. X: chloride=Cl, bromide=Br, iodide=I. L: butylammonium=BA, octylammonium=OA.

Chemicals. When possible, chemicals were purchased from commercial suppliers. The following chemicals were purchased from commercial vendors, stored in a glovebox, and used without further purification. Several additional chemicals critical to the results were synthesized—the details of which are given on the following page.

solvents: N,N-dimethylformamide (DMF) (Sigma-Aldrich, anhydrous, 99.8%), dimethyl sulfoxide (DMSO) (Sigma-Aldrich, anhydrous, ≥99.9%), toluene (Sigma-Aldrich, anhydrous, 99.8%), toluene (Sigma-Aldrich, ≥99.5), acetone (Sigma-Aldrich, ≥99.5%), ethanol (VWR, 100%)

AX: cesium bromide (CsBr) (Sigma-Aldrich, 99.999%), cesium iodide (CsI) (Sigma-Aldrich, ≥99.9995%), methylamine hydrochloride (MACl) (Sigma-Aldrich), methylammonium bromide (MABr) (Sigma-Aldrich), methylammonium iodide (MAI) (Sigma-Aldrich), formamidine acetate salt (Sigma-Aldrich, 99%)

BX$_2$: lead (II) chloride (PbCl$_2$) (Alfa Aesar, 99.999%), lead (II) bromide (PbBr$_2$) (Sigma-Aldrich, 99.999%), lead (II) iodide solution (PbI$_2$), 0.55M in DMF (Sigma-Aldrich), tin (II) iodide (SnI$_2$) (Alfa Aesar, 99.999%)

LX: octylamine (Sigma-Aldrich, 99%), butylamine (Sigma-Aldrich, 99.5%), n-butylammonium iodide (BAI) (Sigma-Aldrich)

acids: hydrochloric acid (HCl) (Sigma-Aldrich, 37%), hydrobromic acid (HBr) (Sigma-Aldrich, 48%), hydriodic acid (HI) (Sigma-Aldrich, 55%)

However, several of the ligand salts (LX) and cation salts (AX) used for perovskite synthesis are not commercially available and were synthesized in-house. In general, this was done by reacting the amine species or the cation salt with a slight excess of the corresponding acid, followed by thorough washing with diethyl ether and recrystallization to purify the compound. For example, octylammonium iodide (OAI) was synthesized by reacting 120 mmol of octylamine with 130 mmol of hydriodic acid (HI) in 100 mL of ethanol. The products were dried using rotary evaporation, washed thoroughly with diethyl ether, and recrystallized once using acetone to produce a white, shiny solid. All chemicals were stored in an oxygen- and water-free glovebox. Full details for the synthesis of each chemical used in this study are provided in the Supporting Information and Table 6.

Table 6 summarizes the synthetic details for each precursor salt. The formamidinium halide salts were prepared without a reaction solvent. In the case of mixed recrystallization solvents, such as acetone/ethanol, acetone was a poor solvent for the salt even near its boiling point, and so a small amount of ethanol was added to aid with dissolution. The octylamine and butylamine used for the synthesis were kept in a glovebox for storage.

Nanoplatelet Synthesis.

Nanoplatelets were synthesized using a non-solvent crystallization method. See, Schmidt, L. C.; Pertegas, A.; González-Carrero, S.; Malinkiewicz, O.; Agouram, S.; Espallargas, G. M.; Bolink, H. J.; Galian, R. E.; Perez-Prieto, J. J. Am. Chem. Soc. 2014, 136, 850-853, Sichert, J. A.; Tong, Y; Mutz, N.; Vollmer, M.; Fischer, S.; Milowska, K. Z.; Cortadella, R. G.; Nickel, B.; Cardenas-Daw, C.; Stolarczyk, J. K.; Urban, A. S.; Feldmann, J. Nano Lett. 2015, 15, 6521-6527, and Pathak, S.; Sakai, N.; Rivarola, F. W. R.; Stranks, S. D.; Liu, J.; Eperon, G. E.; Ducati, C.; Wojciechowski, K.; Griffiths, J. T.; Haghighirad, A. A.; Pellaroque, A.; Friend, R. H.; Snaith, H. J. Chem. Mater. 2015, 27, 8066-8075, each of which is incorporated by reference in its entirety. Syntheses were performed under ambient laboratory conditions, except for those involving tin, which were performed in a glovebox. Stock solutions

TABLE 6

Synthesis parameters for precursor salts.

| precursor salt | reagent 1 | reagent 2 | reaction solvent | recrystallization solvent | reference |
|---|---|---|---|---|---|
| butylammonium chloride (BACl) | butylamine, 120 mmol | hydrochloric acid, 130 mmol | ethanol, 100 mL | acetone/ethanol | — |
| butylammonium bromide (BABr) | butylamine, 120 mmol | hydrobromic acid, 130 mmol | ethanol, 100 mL | acetone | Dou[1] |
| octylammonium chloride (OACl) | octylamine, 120 mmol | hydrochloric acid, 130 mmol | ethanol, 100 mL | acetone/ethanol | Pathak[2] |
| octylammonium bromide (OABr) | octylamine, 42 mmol | hydrobromic acid, 45 mmol | ethanol, 50 mL | acetone | Tyagi[3] |
| octylammonium iodide (OAI) | octylamine, 120 mmol | hydriodic acid, 130 mmol | ethanol, 100 mL | acetone | Pathak[2] |
| formamidinium chloride (FACl) | formamidinium acetate salt, 100 mmol | hydrochloric acid, 100 mmol | — | ethanol | — |
| formamidinium bromide (FABr) | formamidinium acetate salt, 100 mmol | hydrobromic acid, 100 mmol | — | ethanol | Eperon[4] |
| formamidinium iodide (FAI) | formamidinium acetate salt, 100 mmol | hydriodic acid, 100 mmol | — | ethanol | Eperon[4] |

Precursor Salt Preparation.

The preparation of precursor salts were followed from procedures found in literature, when possible. The general preparation is as follows. The amine or cation species were added to a solvent, typically ethanol, in a single-neck round bottom flask. A water bath was placed around this flask. An equimolar (or slight excess) of acid was then added dropwise to the stirring solution using a dropping funnel. The reaction was allowed to proceed for 2 hours at room temperature under ambient conditions. The volatiles were then removed from the products using a rotary evaporator, leaving behind the solids. The solids were washed several times with diethyl ether (at least 3 washing cycles—the precursors prepared from hydriodic acid were washed many times until they no longer had an orange color). The precursors were then recrystallized once (producing a white powder in all cases) and washed a final time with diethyl ether before being brought into an oxygen and water-free glovebox.

were prepared by dissolving precursor salts (AX, BX$_2$, LX) in N,N-dimethylformamide (DMF), typically at concentrations of 0.1M. The stock solutions were then mixed in proper proportions to obtain either n=1 or n=2 thickness nanoplatelets. For ease of calculating the mixing ratios, the formula for the nanoplatelets can be rewritten in terms of their precursor salts: $(LX)_2(BX_2)_n(AX)_{n-1}$. Hence, for n=1 nanoplatelets, the stoichiometry calls for a ratio of 2:1:0 (LX:BX$_2$:AX) and a ratio of 2:2:1 for n=2 nanoplatelets. However, in this study an excess of ligands were used for the n=2 nanoplatelets (typically 10:2:1 LX:BX$_2$:AX) to achieve better thickness homogeneity and colloidal stability (see FIG. 14).

In all cases a 50/50 mixture of octylammonium (OA) and butylammonium (BA) was used as the ligand species L, which results in better thickness homogeneity. It is hypothesized that octylammonium alone may be too bulky to bind to every site on the nanoplatelet surface and so the addition of butylammonium can help to better passivated the nanoplatelets and prevent growth to thicker nanoplatelets. For example, the precursor mixture for the synthesis of $L_2[FAPbBr_3]PbBr_4$ was 5 parts octylamonium bromide (OABr), 5 parts butylammonium bromide (BABr), 2 parts lead bromide ($PbBr_2$), and 1 part formamidinium bromide (FABr). The precursor solution was added dropwise to toluene undergoing vigorous stirring at room temperature (see Synthesis details below). The nanoplatelets form immediately, as evidenced by the appearance of photoluminescence. For this study, a single drop of precursor solution (~10 μL) was added to 10 mL of toluene. Larger quantities of nanoplatelets can be produced by adding additional precursor drops or using higher concentration precursor stock solutions (0.5M, 1.0M). However, dropwise precursor addition can slightly redshift the emission peak with each drop, so a single precursor addition was used throughout this work. See the Supporting Information for additional details related to synthesis.

Synthesis Details.

Syntheses were performed under ambient laboratory conditions, except for those involving tin, which were performed in a glovebox. Stock solutions were prepared by dissolving precursor salts (AX, $BX_2$, LX) in N,N-dimethylformamide (DMF), typically at concentrations of 0.1M. Stock solutions were prepared in a glovebox (using chemicals and anhydrous DMF from the glovebox) and then removed for use. In the case of CsBr, which was not soluble in DMF, the salt was dissolved in DMSO. The $PbCl_2$ and $PbBr_2$ solutions were heated to 80° C. to ensure full dissolution in the DMF. For $PbI_2$ solutions, a 0.55M solution of $PbI_2$ in DMF which is commercially available from Sigma-Aldrich was used, as it was difficult to completely dissolve solid $PbI_2$ in DMF at all concentrations desired.

The stock precursor solutions were then mixed in proper proportions to obtain either n=1 or n=2 thickness nanoplatelets. The stoichiometry calls for a 2:1:0 ratio of $LX:BX_2:AX$ for n=1 nanoplatelets and a ratio of 2:2:1 of $LX:BX_2:AX$ for n=2 nanoplatelets. Experimentally, a ratio of 10:2:1 $LX:BX_2:AX$ was used for the n=2 nanoplatelets to achieve better thickness homogeneity and colloidal stability (see FIG. 14). The excess of the ligands, L, helps to prevent growth to thicker nanoplatelets and ensures only n=2 is produced. In all cases a 50/50 mixture of octylammonium (OA) and butylammonium (BA) were used as the ligand species L. Therefore, those solutions are 0.05M OA, 0.05M BA for a total ligand concentration of 0.1M.

Figure 9:
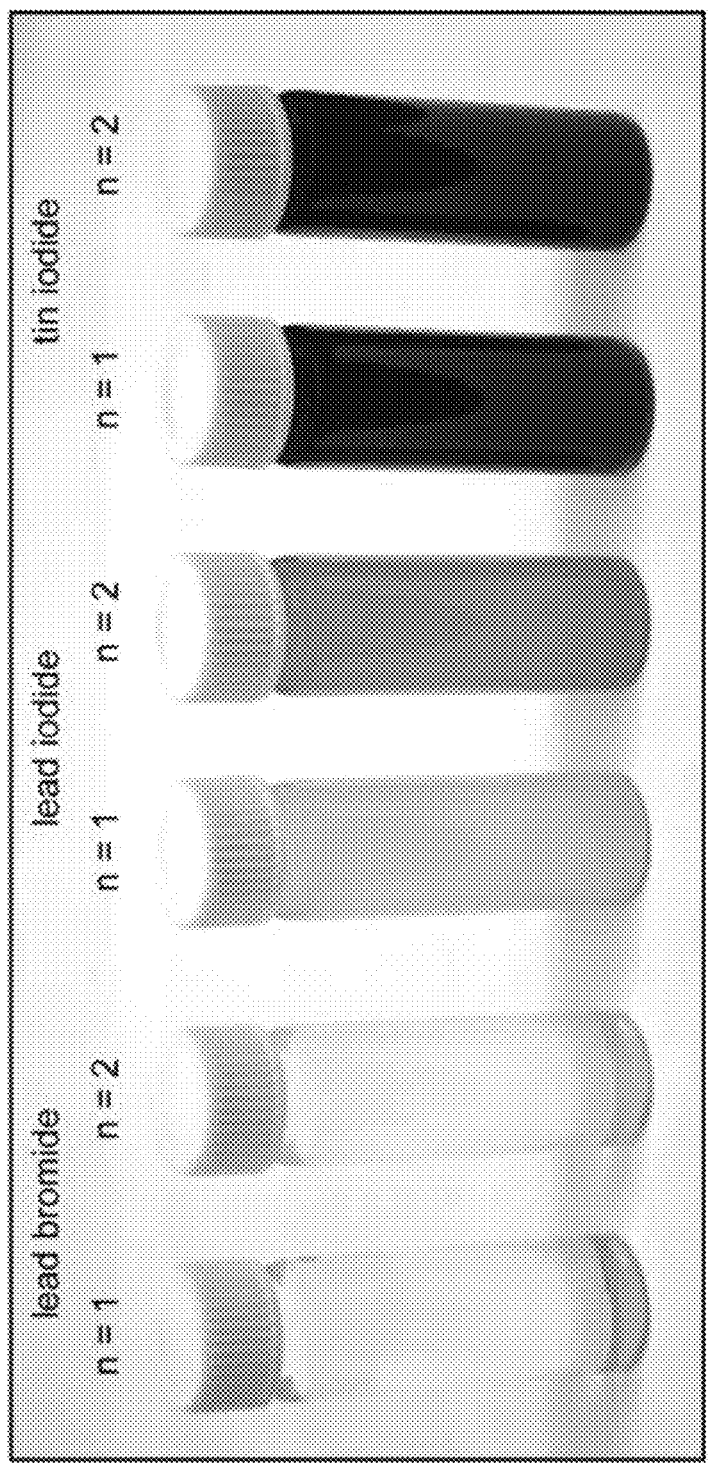
FIG. 9 shows nanoplatelet suspensions in toluene under ambient lighting.

The precursor solution was added dropwise to 10 mL of toluene undergoing stirring at room temperature. The nanoplatelets form immediately, as evidenced by the presence of photolumi-nescence. For this study, a single drop of precursor solution (~10 μL) was added to the toluene phase. Larger quantities of nanoplatelets can be produced by adding additional precursor drops or using higher concentration precursor solutions (0.5M, 1.0M). However, dropwise precursor addition can red-shift the emission peak by a few nanometers with additional drops and so a single precursor addition was used in this work. These results indicate that partial growth in the confined dimension of existing nanoplatelets may be occurring during the addition of subsequent precursor amounts. While significant changes were not observed in the lateral dimensions of the nanoplatelets with addition of precursor, the photoluminescence indicates that slight growth in this thickness-confined direction of the nanoplatelets is occurring. These results pose a problem for scale-up of this synthesis, as the energy of emission is somewhat dependent on the scale of the crystallization. Further work is needed to address this issue; early signs show that it may be a synthesis which is best suited for continuous rather than batch fabrication. In FIG. 9, nanoplatelets were made using 0.5M precursor solutions except for the tin iodide nanoplatelets, which were made using 5M solutions.

Tin-based perovskites were synthesized in the same manner, however, all steps were performed in an oxygen and water free glovebox (oxygen<10 ppm, water<1 pmm), as the materials are highly sensitive to degradation by exposure to ambient conditions. The tin-based nanoplatelets do not crystallize as readily as lead-based nanoplatelets and so typically a 1M or 5M basis was used for all of the precursor salt solutions. n=1 ($L_2SnI_4$) and n=2 ($L_2[FASnI_3]SnI_4$) tin-based perovskite nanoplatelets are dark red and black, respectively, which allows a straightforward determination of a successful synthesis. However, under several circumstances transparent, broad-emitting particles can form instead of the desired tin-based nanoplatelets. Undesirable conditions under which the formation of these transparent particles was observed are summarized here:

1. Using dilute stock solutions: 1M or more concentrated stock solutions should be used for the tin-based synthesis.

2. Using too many ligands (L) for the precursor mixture ($LI:SnI_2:FAI$): For 1M and 5M stock solutions, no more than 3 or 5 parts of ligands (3:2:1 and 5:2:1), respectively, could be used for the synthesis of n=2 nanoplatelets.

3. Dilution of successfully synthesized nanoplatelets in additional toluene: Addition of toluene often triggers the transition from nanoplatelets to the transparent particles.

4. Increased temperature during the synthesis by heating toluene with a hotplate.

5. Air exposure for some seconds or minutes.

Figure 10B:
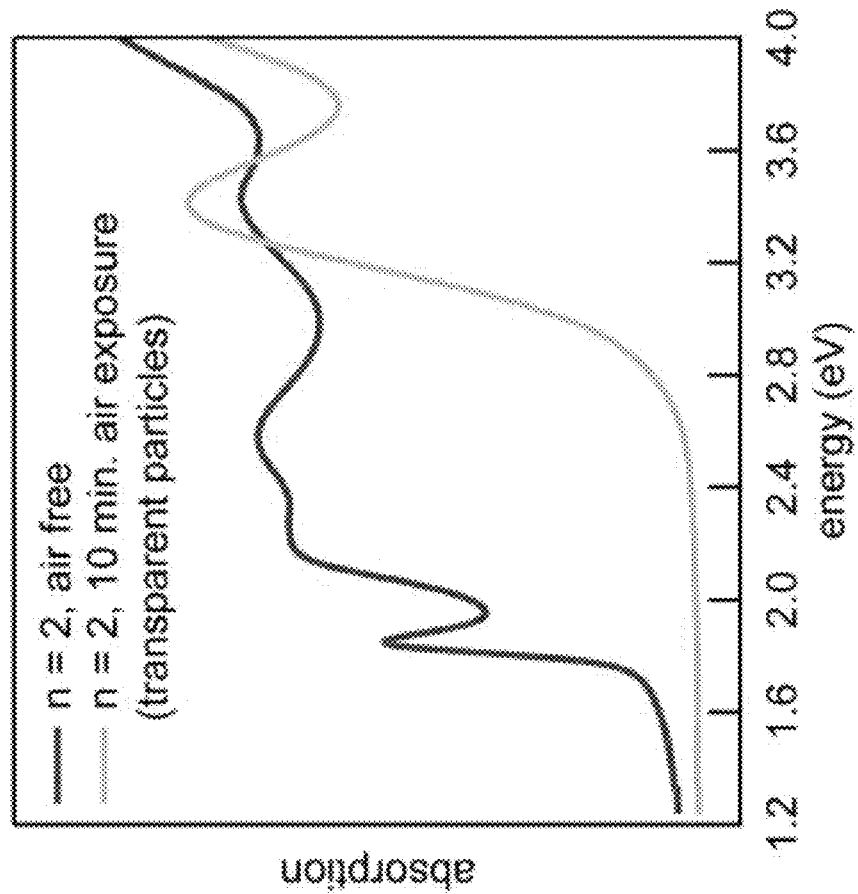
FIG. 10B shows absorption spectra of n=2 nanoplatelets as compared with the transparent particles.
Figure 10A:
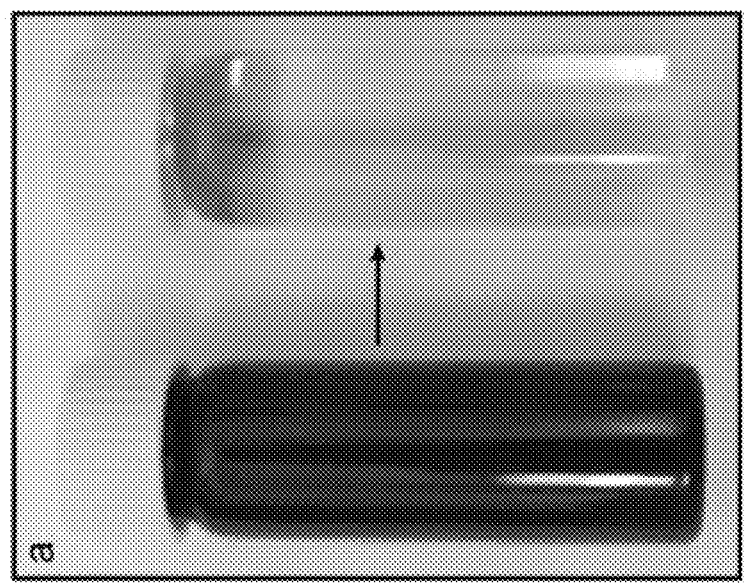
FIGS. 10A and 10C show photographs of tin-based nanoplatelets undergoing transformation to the transparent particle phase under ambient light (FIG. 10A), under ultraviolet light (FIG. 10C).
Figure 10D:
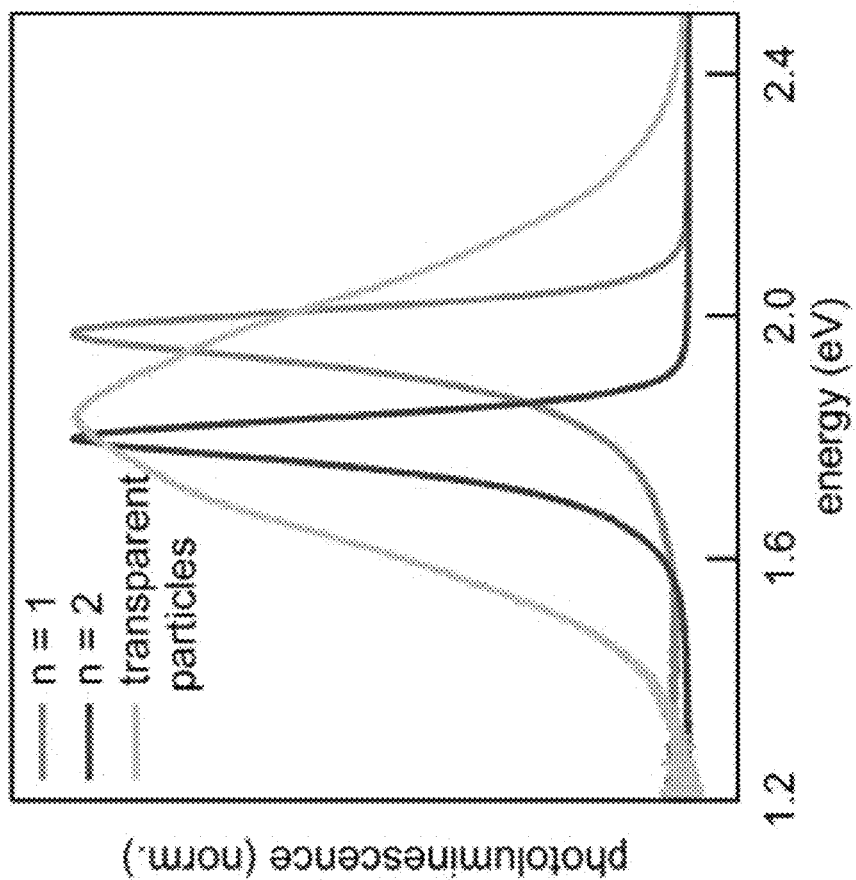
FIG. 10D shows photoluminescence spectra of n=1 and n=2 nanoplatelets as compared with the transparent particle photoluminescence.
Figure 10C:
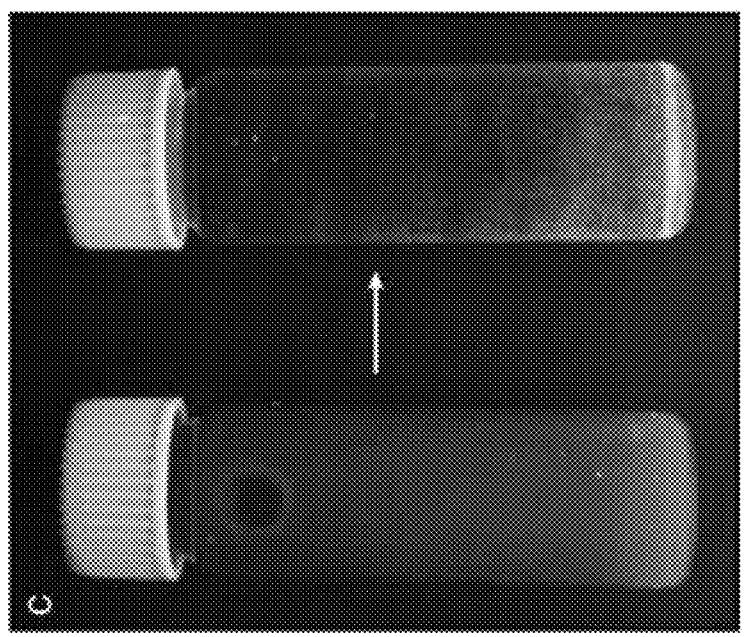

The transparent particles can form either directly when adding a precursor drop to toluene or after a successful synthesis (solutions turn transparent after being dark-red/black (FIGS. 10A and 10B). Other than their transparency, the particles exhibit a characteristic orange fluorescence, as shown in FIGS. 10C and 10D. The exact origin and composition of the transparent particles is unclear. However, in bulk tin-based perovskites a "self-doping" from $Sn^{2+}$ to $Sn^{4+}$ has been reported by Takahashi et al. See, Takahashi, Y.; Obara, R.; Lin, Z.; Takahashi, Y.; Naito, T.; Inabe, T.; Ishibashi, S.; Terakura, K. *Dalton Trans.* 2011, 40, 5563-5568, which is incorporated by reference in its entirety. Similarly, the loss of all excitonic feature in the optical absorption spectra has been reported for tin-based perovskite nanocrystals by Jellico et al. and for $L_2SnI_4$ layered perovskites by Xu et al. See, Xu, Z.; Mitzi, D. B.; Medeiros, D. R. *Inorg. Chem.* 2003, 42, 1400-1402, which is incorporated by reference in its entirety.

Post-Synthesis Processing.

Figure 8:
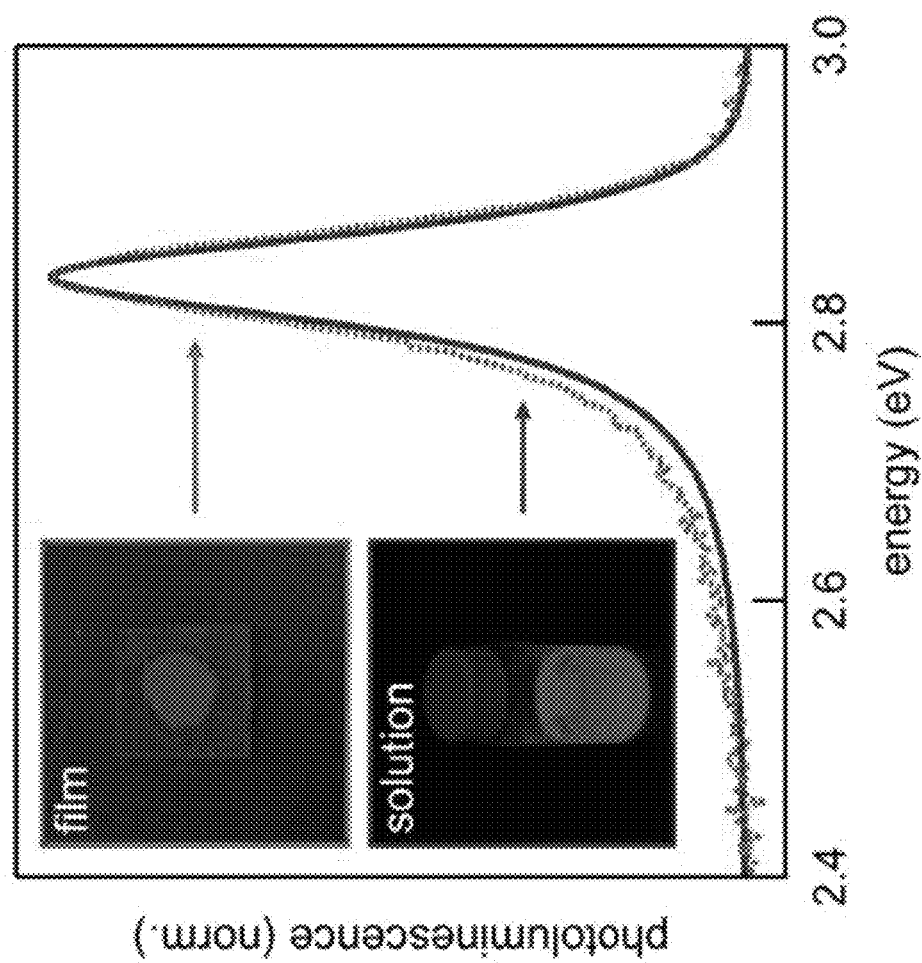
FIG. 8 shows solution and thin film photoluminescence for $L_2[FAPbBr_3]PbBr_4$ nanoplatelets. Insets show photographs of samples under an ultraviolet lamp.

The majority of data presented were collected in solution phase, using as-synthesized nanoplatelets in toluene. Nanoplatelets could be isolated from the toluene/DMF growth solution by centrifugation. Typically, the nanoplatelets in solution were centrifuged at 4000 rpm for 5 minutes or longer, leading to at least partial precipitation. The nanoplatelets can then be redispersed in organic solvents and drop-cast into thin films (see FIG. 8). This process typically reduces the emission brightness of the nanoplatelets, which may be due to a loss of ligand coverage or exposure to oxygen and water when in the solid state. See the Supporting Information for a discussion of challenges related to nanoplatelet stability.

Characterization.

Photoluminescence and absorption spectra were recorded using an Avantes fiber optic spectrometer and Cary 5000

UV-Vis spectrophotometer, respectively. Samples were excited by a 365 nm fiber-coupled LED (Thorlabs) for photoluminescence measurements. Before analysis, photoluminescence spectra were converted to an energy scale using the procedure outlined by Mooney & Kambhampati. See, Mooney, J.; Kambhampati, P. J. Phys. Chem. Lett. 2013, 4, 3316-3318, which is incorporated by reference in its entirety. Transmission electron microscopy (TEM) was performed on a JEOL 2011 operating at 200 kV. TEM samples were prepared by centrifuging the reaction products to precipitate the nanoplatelets, redispersing in a small quantity of toluene (~250 μL), and drop-casting onto a carbon film TEM grid. X-ray diffraction (XRD) was performed using a PANanlytical X'Pert PRO operating at 45 kV and 40 mA using a copper radiation source. XRD samples were prepared by centrifuging reaction products (made using 0.5M stock solutions), redispersing in a small quantity of toluene (~30 μL), and drop-casting onto glass slides. Tin-based samples were measured using an air-free sample holder. Substrate background scatter was subtracted from XRD patterns using HighScore Plus software. PLQY measurements were performed using an integrating sphere and CCD spectrograph (Princeton Instruments). See, deMello, J. C.; Wittmann, H. F.; Friend, R. H. Adv. Mater. 1997, 9, 230-232, which is incorporated by reference in its entirety. Samples were excited using a 405 nm laser (PicoQuant). The relative efficiency of the detection system was determined using a calibrated tungsten halogen lamp. All samples had optical densities below 0.1 at 405 nm for these measurements, except for the tin-based perovskites, which transformed into an undesired phase if diluted (see Supplementary Information) and so were measured with optical densities>1.

Stability of Nanoplatelets.

Figure 11:
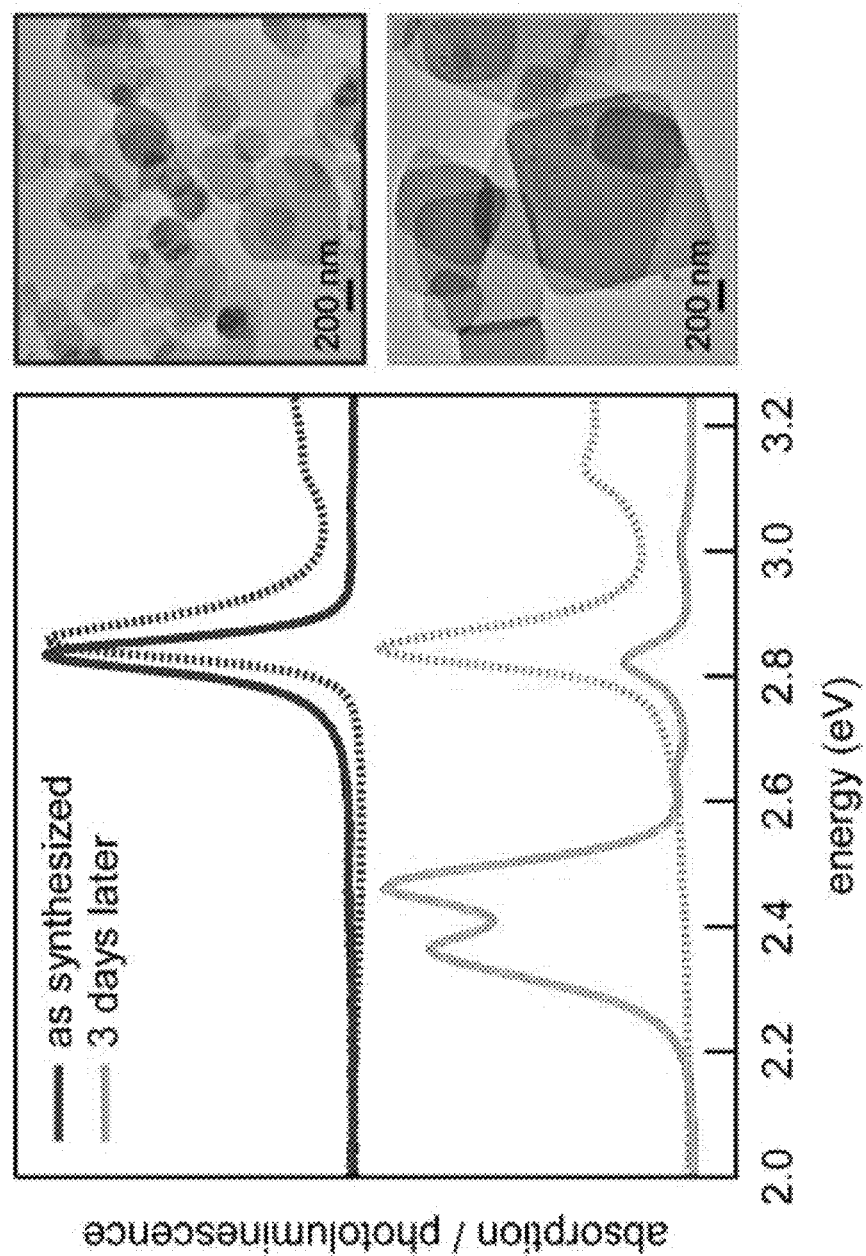
FIG. 11 shows changes in the photoluminescence of $L_2[FAPbBr_3]PbBr_4$ nanoplatelets after several days under ambient conditions and the corresponding TEM images of these samples.

The nanoplatelets synthesized here generally (excluding tin-based nanoplatelets) show stability over the course of several days. Cesium nanoplatelets are a notable exception, as they typically evolve into thicker nanoplatelets over several minutes to hours, which is attributed to the smaller size of the cesium cation and increased diffusivity. However, there are several other observations related to stability. The first is related to lead bromide nanoplatelets of thickness n=2 ($L_2[APbBr_3]PbBr_4$). The photoluminescence spectrum evolves after several days from one characteristic of n=2 thickness (440 nm) to one characteristic of a mixture of thicker nanoplatelets (510-530 nm). The effect is illustrated in FIG. 11. TEM images of as-synthesized nanoplatelets compared to 3 days post-synthesis shows that the nanoplatelets have grown in lateral dimension and likely in thickness, as evidenced by the increased contrast of the nanoplatelets (and revealed by the photoluminescence spectrum). This effect is most pronounced for formamidinium-based nanoplatelets but also can occur in methylammonium-based nanoplatelets. Interestingly, the absorption remains relatively unchanged during the changes to the photoluminescence.

Figure 12:
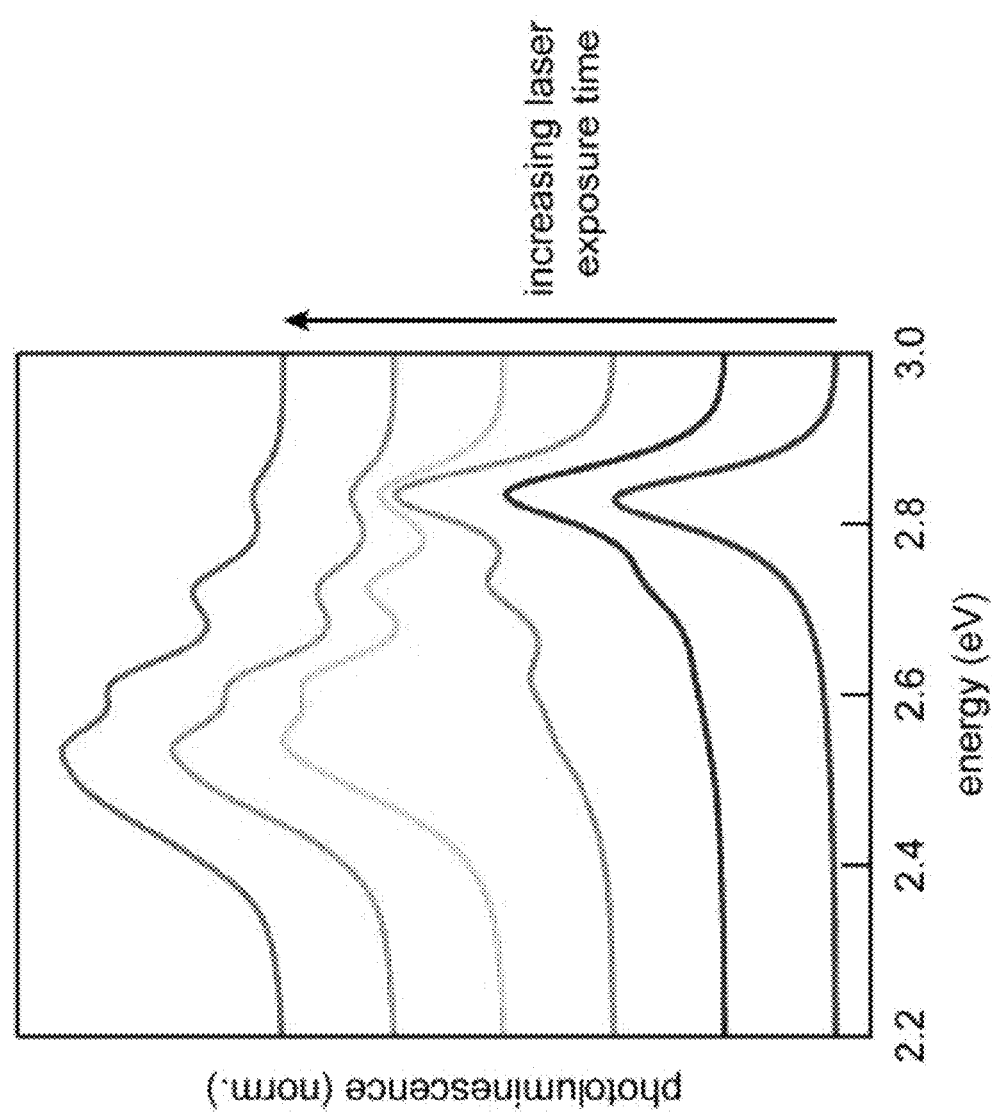
FIG. 12 shows evolution of $L_2[MAPbBr_3]PbBr_4$ nanoplatelets to thicker nanoplatelets and bulk-like phases under constant laser illumination (10 mW, 365 nm).

Evolution to thicker and bulk-like particles can be caused by high ultraviolet light intensity (~5-10 mW). Therefore, samples should not be exposed to excessive intensity while measuring photoluminescence (see FIG. 12). In FIG. 12, the changes occur over the course of approximately 15 minutes. Notably, the areas of a drop-cast film which have the thinnest coverage will photoluminesce green before the thicker areas, which continue to photoluminesce blue. This indicates that exposure to oxygen and/or water is likely the driving force behind the transformation.

Lastly, the purification of nanoplatelets, as has been noted previously in several studies, can be challenging. The nanoplatelets are susceptible to re-dissolution in polar solvents, like those typically used in purification for colloidal destabilization. In this work, the use of polar solvents was avoided and instead longer centrifugation times was used in order to precipitate the nanoplatelets from the as-synthesized solution. Typically colloidal stability and photoluminescence brightness are lower after centrifugation and redispersal. However, the non-solvent crystallization method outlined here should produce fairly pure nanoplatelets as-synthesized. Unlike high-temperature syntheses, there are no high boiling point solvents used in the synthesis or large excesses of ligand species. The products synthesized here consist of: nanoplatelets, toluene, and very small quantities of DMF and ligands. DMF is the main impurity to consider, as it has the potential to re-dissolve the nanoplatelets.

Other embodiments are within the scope of the following claims.

What is claimed is:

1. A composition comprising:
one or more of a colloidal nanoplatelet of the formula (I):

$$L_2[ABX_3]_{n-1}BX_4 \qquad (I)$$

wherein L is an organic ligand or combination thereof, A is a monovalent metal or organic molecular cation, B is a divalent metal cation, X includes a halide or combinations thereof, and n−1 is the number of unit cells in thickness, wherein n is 1, 2, 3 or 4, wherein L is a mixture of two different organic ligands or X is a mixture of two different halide ions when A is methylammonium and B is Pb.

2. The composition of claim 1, wherein the organic ligand includes octylammonium (OA) or butylammonium (BA).

3. The composition of claim 1, wherein the monovalent metal or organic molecular cation includes cesium (Cs), methylammonium (MA) or formamidinium (FA).

4. The composition of claim 1, wherein the divalent metal cation is lead (Pb) or tin (Sn).

5. The composition of claim 1, wherein the halide anion is chloride (Cl), bromide (Br), iodide (I), or combinations thereof.

6. The composition of claim 1, wherein the n is 1 or 2.

7. The composition of claim 1, wherein a peak absorption wavelength of the composition is between near-IR and UV.

8. A light-emitting diode comprising the composition of claim 1.

9. A solar cell comprising the composition of claim 1.

10. A method of modulating an absorption and emission spectrum of a composition comprising:
selecting a peak absorption wavelength between near-IR and UV;
synthesizing a mixture of one or more colloidal nanoplatelets of the formula (I):

$$L_2[ABX_3]_{n-1}BX_4 \qquad (I)$$

wherein L is an organic ligand or combinations thereof, A is a monovalent metal or organic molecular cation, B is a divalent metal cation, X is a halide anion, and n−1 is the number of unit cells in thickness, wherein n is 1, 2, 3 or 4 and wherein the halide anion is chloride (Cl), bromide (Br), iodide (I), or combinations thereof, wherein L is a mixture of two different organic ligands or X is a mixture of two different halide ions when A is methylammonium and B is Pb; and
wherein the mixture has the selected peak absorption wavelength.

11. The method of claim 10, wherein the organic ligand includes octylammonium (OA) or butylammonium (BA).

12. The method of claim 10, wherein the monovalent metal or organic molecular cation includes cesium (Cs), methylammonium (MA) or formamidinium (FA).

13. The method of claim 10, wherein the divalent metal cation is lead (Pb) or tin (Sn).

14. The method of claim 10, wherein then is 1 or 2.

* * * * *